US012370251B2

(12) United States Patent
Blackburn et al.

(10) Patent No.: US 12,370,251 B2
(45) Date of Patent: Jul. 29, 2025

(54) ADJUVANTED NANOPARTICULATE INFLUENZA VACCINE

(75) Inventors: Peter Blackburn, Scarsdale, NY (US); Stephen Grimes, Scarsdale, NY (US)

(73) Assignee: MERCIA PHARMA, INC., New York, NY (US)

( * ) Notice: Subject to any disclaimer, the term of this patent is extended or adjusted under 35 U.S.C. 154(b) by 0 days.

(21) Appl. No.: 13/505,971

(22) PCT Filed: Nov. 5, 2010

(86) PCT No.: PCT/US2010/002903
§ 371 (c)(1),
(2), (4) Date: May 3, 2012

(87) PCT Pub. No.: WO2011/056226
PCT Pub. Date: May 12, 2011

(65) Prior Publication Data
US 2012/0219605 A1  Aug. 30, 2012

Related U.S. Application Data

(60) Provisional application No. 61/258,332, filed on Nov. 5, 2009.

(51) Int. Cl.
| | | |
|---|---|---|
| A61K 39/145 | (2006.01) |
| A61K 9/107 | (2006.01) |
| A61K 39/00 | (2006.01) |
| A61K 39/12 | (2006.01) |
| A61K 39/39 | (2006.01) |
| A61P 31/16 | (2006.01) |
| A61P 37/04 | (2006.01) |

(52) U.S. Cl.
CPC ............ *A61K 39/145* (2013.01); *A61K 39/12* (2013.01); *A61K 39/39* (2013.01); *A61K 2039/55555* (2013.01); *A61K 2039/55566* (2013.01); *A61K 2039/58* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 3,983,228 A | | 9/1976 | Woodhour et al. |
| 4,073,743 A | * | 2/1978 | Midler et al. ............. 424/209.1 |
| 5,109,026 A | * | 4/1992 | Hoskinson ............. A61K 39/39 514/939 |
| 5,744,137 A | * | 4/1998 | Stone ................... A61K 9/1075 514/939 |
| 6,197,926 B1 | | 3/2001 | Gaur et al. |
| 7,122,191 B2 | | 10/2006 | Dominowski et al. |
| 7,785,603 B2 | | 8/2010 | Luke et al. |
| 7,824,864 B2 | | 11/2010 | Alving et al. |
| 2002/0058040 A1 | * | 5/2002 | Grimes et al. ............. 424/185.1 |
| 2003/0049797 A1 | | 3/2003 | Yuki et al. |
| 2005/0220814 A1 | | 10/2005 | Dominowski et al. |
| 2006/0121055 A1 | * | 6/2006 | Campbell ............ A61K 31/716 424/209.1 |
| 2006/0160160 A1 | | 7/2006 | Alving et al. |
| 2007/0225210 A1 | | 9/2007 | Blackburn |
| 2008/0014217 A1 | | 1/2008 | Hanon et al. |
| 2008/0057080 A1 | | 3/2008 | Luke et al. |
| 2010/0048452 A1 | * | 2/2010 | Gaucheron ............ A61K 9/107 514/786 |

FOREIGN PATENT DOCUMENTS

| | | | |
|---|---|---|---|
| FR | 2903602 A1 * | 1/2008 | ........... A61K 9/0019 |
| WO | WO 1994/007530 | 4/1994 | |
| WO | WO 99/61916 | 12/1999 | |
| WO | WO 2001/031037 | 5/2001 | |
| WO | WO 2001/045670 | 6/2001 | |
| WO | WO 2004/060396 | 7/2004 | |
| WO | WO 2010/016912 | 2/2010 | |

OTHER PUBLICATIONS

Aucouturier, Jerome, et al. "Montanide ISA 720 and 51: a new generation of water in oil emulsions as adjuvants for human vaccines." Expert review of vaccines 1.1 (2002): 111-118. (Year: 2002).*
Fox, Christopher B. "Squalene emulsions for parenteral vaccine and drug delivery." Molecules 14.9 (Sep. 1, 2009): 3286-3312. (Year: 2009).*
International Search Report and Written Opinion of the US Searching Authority for International Application No. PCT/US2010/02903 dated Dec. 20, 2010.
Koh, Yi T., et al., "Immunological Consequences of Using Three Different Clinical/Laboratory Techniques of Emulsifying Peptide-Based Vaccines in Incomplete Freund's Adjuvant", Journal of Transitional Medicine, (2006), vol. 4, pp. 42, doi:10.1186/1479-5876-4-42.
Sasaki, Takashi, et al., "Evaluation of the Potency, Optimal Antigen Level and Lasting Immunity of Inactivated Avian Influenza Vaccine Prepared from H5N1 Virus", Japanese Journal of Veterinary Research, vol. 56, No. 4, pp. 189-198, (2009).
Alleva et al., Immunological Characterization and Therapeutic Activity of an Altered-Peptide Ligand, NBI-6024, Based on the Immunodominant Type 1 Diabetes Autoantigen Insulin B-Chain (9-23) Peptide, Diabetes 51:2126-2134 (2002).
Miles et al., Montanide ISA 720 vaccines: quality control of emulsions, stability of formulated antigens, and comparative immunogenicity of vaccine formulations, Vaccine 23(19):2530-2539 (2005).

(Continued)

*Primary Examiner* — Bethany P Barham
*Assistant Examiner* — Peter Anthopolos
(74) *Attorney, Agent, or Firm* — Hoxie & Associates LLC

(57) ABSTRACT

Vaccine compositions comprising influenza antigens formulated as nanoparticulate water in oil miniemulsions. The vaccines may be formulated at the point of use and are useful in emergency response conditions.

20 Claims, 9 Drawing Sheets

(56) References Cited

OTHER PUBLICATIONS

Figure 1:
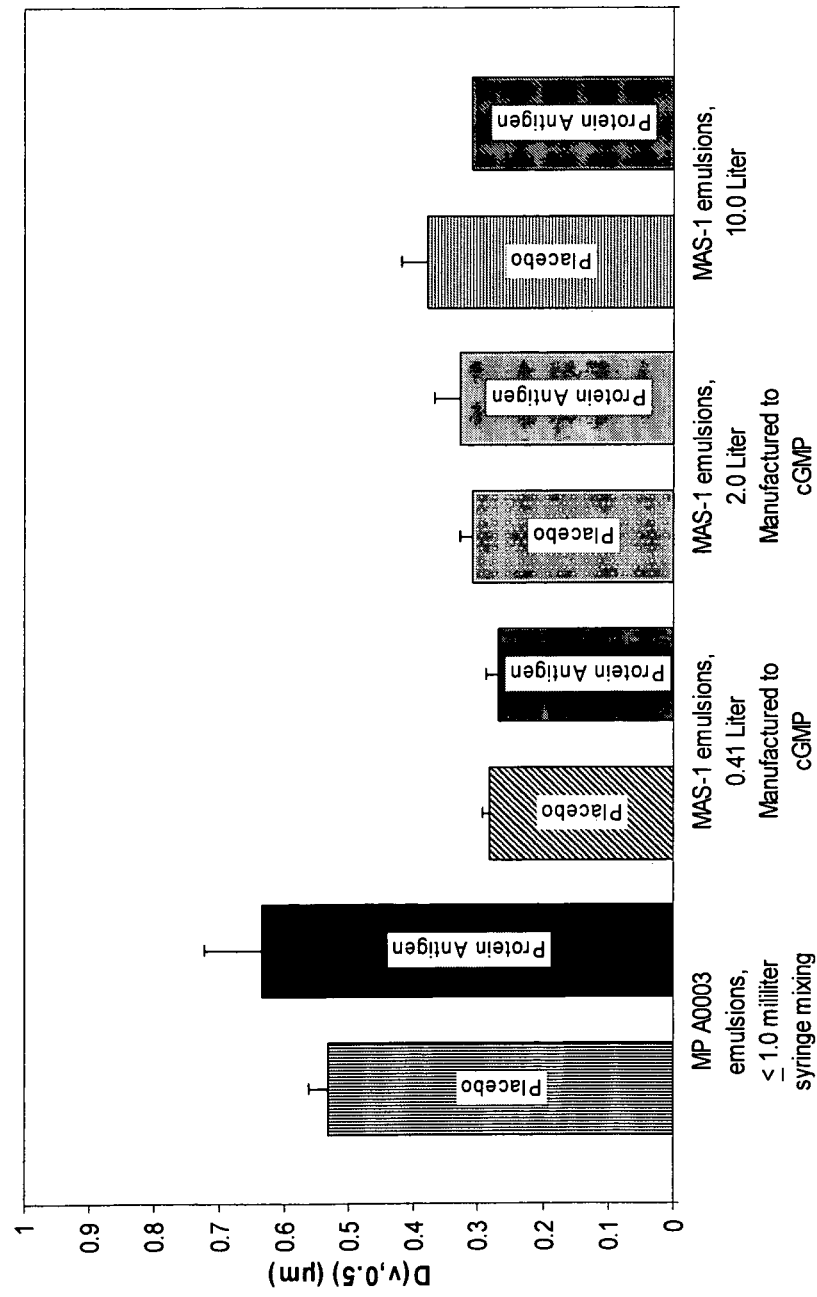

Myc et al., Development of immune response that protects mice from viral pneumonitis after a single intranasal immunization with influenza A virus and nanoemulsion, Vaccine 21(25-26):3801-3814 (2009).
Zimmerman et al., Enhanced immunogenicity of avian influenza antigen H5 by addition of CEL-1000 to MAS-1 (Presentation No. E-071; Poster Board No. 229), Abstracts of the General Meeting of the American Society for Microbiology; $107^{th}$ General Meeting of the American-Society-for-Microbiology, American Society for Microbiology (2007) Abstract Only.
Zimmerman et al., Importance of Timing of CEL-1000 Treatment for Optimizing Antibody Response to Recombinant HBV Antigen with MAS-1 Adjuvant, Abstracts Book, Interscience Conference on Antimicrobial Agents & Chemotherapy (ICAAC); $47^{th}$ Interscience Conference on Antimicrobial Agents and Chemotherapy; American Society for Microbiology (2007) Abstract Only.
Isoda et al., "Potency of an inactivated avian influenza vaccine prepared from a non-pathogenic H5N1 reassortant virus generated between isolates from migratory ducks in Asia," Arch. Virol., 153: 1685-1692 (2008).
Podda, "The adjuvanted influenza vaccines with novel adjuvants: experience with the MF59-adjuvanted vaccine," *Vaccine*, 19:2673-2680 (2001).
PubChem CID 66969154, 11 pages, (2012); retrieved on Jan. 4, 2021 from https://pubchem.ncbi.nlm.nih.gov/compound/Unii-A2SV334fma.
PubChem CID 25262459, 11 pages, (2009); retrieved on Jan. 4, 2021 from https://pubchem.ncbi.nlm.nih.gov/compound/25262459.

* cited by examiner

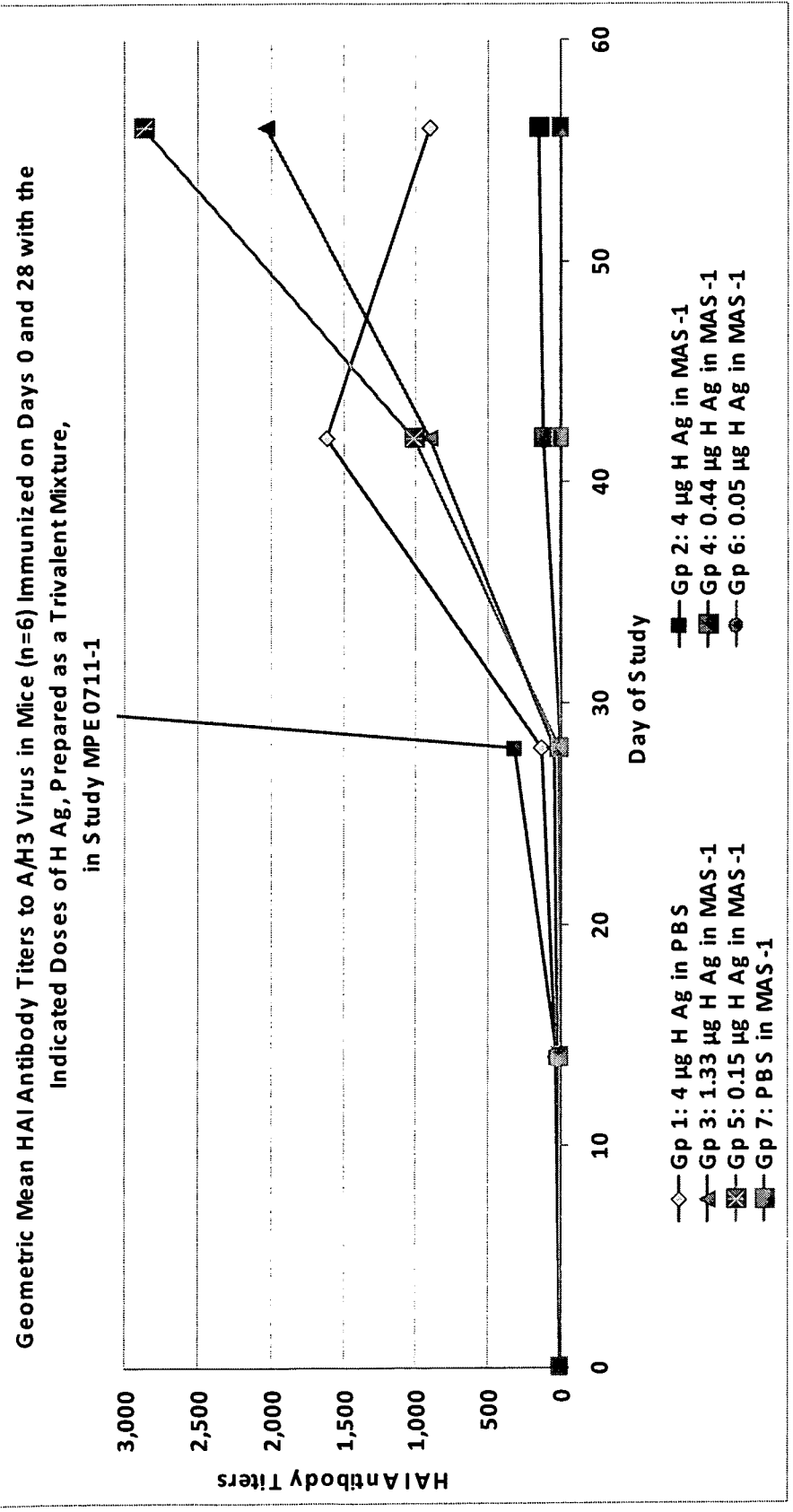

ADJUVANTED NANOPARTICULATE INFLUENZA VACCINE

CROSS REFERENCE TO RELATED APPLICATIONS

This application is a United States Application under 35 C.F.R. 371 claiming benefit of PCT Application No. PCT/US2010/002903, filed on Nov. 5, 2010, which claims the benefit of U.S. Provisional Application No. 61/258,332, filed on Nov. 5, 2009, the contents of each of which are incorporated herein by reference.

STATEMENT REGARDING GOVERNMENT FUNDING

This invention was supported in part with government support under Grant No. R43A1074119 awarded by the National Institute of Allergy and Infectious Diseases. The government has certain rights in the invention.

TECHNICAL FIELD

The field relates to compositions involving prophylactic nanoparticulate influenza vaccines. The field further relates to natural adjuvants used in conjunction with prophylactic nanoparticulate influenza vaccines. The field also relates to point of use kits that comprise prophylactic nanoparticulate influenza vaccines and natural adjuvants. As well, the field also relates to methods of using said prophylactic nanoparticulate influenza vaccines that comprise natural adjuvants.

BACKGROUND

Seasonal influenza constitutes a significant healthcare problem in the U.S., with an estimated 17 to 50 million persons affected yearly. Influenza was responsible for an average of 36,000 deaths annually throughout the decade 1990-1999, and up to 1 million deaths worldwide. Elderly patients are at particular risk, accounting for 80-90% of influenza related deaths. In the US, the economic cost of the annual flu season is estimated at $71-167 billion (WHO, 2003). Moreover, pandemic influenza, caused by strains of virus that have undergone antigenic shift to produce a new strain against which there is no pre-existing immunity in the human population, can have a catastrophic impact on society. There were three such pandemics in the $20^{th}$ century (1918, 1957, 1968). Over 20 million deaths worldwide were attributed to the pandemic that began in 1918.

The principal means of preventing influenza and of reducing its complications is by vaccination (Nichol, K. L. and Treanor, J. J., 2006). The seasonal influenza vaccine is composed of three strains of virus, comprising one representative strain from each of the principal viral types predominantly responsible for annual global influenza outbreaks since 1977, including A (H1N1), A (H3N2) and B. There are two classes of influenza vaccine, including trivalent inactivated vaccine (TIV), given by intramuscular (IM) injection to individuals aged 6 months and older, and live attenuated influenza virus vaccine (LAIV), administered intranasally in healthy, non-pregnant persons aged 2-49 (ACIP, 2008/9).

Annual adjustments to the composition of the vaccines are necessary to provide protection against seasonal variances in antigenic structure due to viral antigenic drift. Vaccine composition is based on predictions of which strains are likely to be the most prevalent in the next flu season. Occasionally, a different strain circulates than those included in the vaccine, resulting in an increased risk of vaccinees contracting influenza. Such was the case in the 2003-4 flu season in the U.S., when influenza strains related to the prototypical A/Fujuan/411/2002 (H3N2) were circulating whereas the vaccine contained the partly cross-reactive A/Panama/2007/99 (H3N2) viral antigens (Treanor, J., 2004). The current seasonal influenza vaccines provide partial to no cross protection against viral strains not included in the vaccine. A vaccine formulation with greater potency, which was capable of eliciting antibodies cross-reactive against antigenically dissimilar vital strains, and/or against less antigenic epitopes shared by different viral strains, would help compensate for these shortcomings in specificity associated with the present vaccines.

Patient age affects the level of protection obtained from vaccination with TIV (LAIV is not approved for use in the elderly). In adults younger than 65 years of age who are inoculated with TIV that is an antigenic match to circulating virus, clinical efficacy levels of 70-90% are obtained (Podda, A., 2001 and Demicheli. V., 2007). However, in adults older than 65, the TIV clinical efficacy rate drops considerably, to an estimated 30-40% (Goodwin, K., et al., 2006). This has been attributed to the failure of TIV to significantly reduce infection rates in the elderly, probably as a consequence of lower response rates and antibody titers in that age group (Betts, R. F. and Treanor, J. J., 2000). Age related decline in the immune system underlies the reduced immune response to influenza vaccines. However, active immunization remains the most effective measure to prevent influenza and its complications in the elderly. A vaccine that increases efficacy in the elderly, and otherwise immunocompromized individuals, would therefore be of significant benefit to elderly and immunocompromized individuals and society at large.

At present, about 425 million doses of TIV are produced annually, although this is still only sufficient to immunize 7% of the world's population (Layne et al., 2009). An additional drawback of the present vaccine is that shortfalls in production can result in insufficient supplies of vaccine, potentially leaving at-risk patients unprotected. Such occurred in the 2004-5 influenza season, following the discovery of contamination in vaccine lots made at a key manufacturing facility in Liverpool, UK., and subsequent destruction of vaccine lots produced at that facility. Although, shortcomings at the Liverpool facility have been corrected and additional manufacturing sites are under construction, there is still potential for shortfalls in the future. Moreover, there may not be sufficient time to produce enough vaccine for newly emergent strains. This would be particularly serious in the instance of virus emanating from antigenic shift, which has the potential to cause a pandemic. Influenza vaccine with enhanced immunopotency could enable a reduction in the quantity of influenza antigen on a per dose basis, especially in vaccine administered to young healthy adults, who typically mount a vigorous response to vaccination. Such dose-sparing capability would help ensure adequate vaccine supply to protect the population in the event of antigen shortages. Pre-positioned, "point-of-use" presentations of suitable adjuvant would further extend utility of the vaccine.

A vaccine that increases efficacy in the elderly, or otherwise immunocompromized, would be of significant benefit. Moreover, the enhanced immunopotency could induce antibodies against antigenically dissimilar viral strains, and/or against less dominant epitopes, thereby increasing the potential for cross-immunoprotection against other strains of influenza virus not included in the vaccine. In addition, an influenza vaccine with greater immunopotency than the existing vaccines would have a significant beneficial impact where vaccine supplies are scarce since it could result in a dose-sparing effect, which would stretch vaccine stocks to help ensure sufficient supplies to protect the large populations.

The development of adjuvanted vaccines represents a promising strategy enhance immunogenicity and thereby overcome the limitations of influenza vaccine for protection of the elderly, vaccine scarcities, and cross-protection against alternative strains of influenza virus. Recognition of these potential benefits has led to extensive efforts directed at developing adjuvants acceptable for use in man (Palese, T., 2006), including assessments of adjuvanted influenza vaccine in human clinical trials.

The first strong adjuvant to undergo extensive human testing with viral vaccines was Incomplete Freund's Adjuvant (IFA) (Hilleman, M. R., 1968). Freund's adjuvant is the best known of a general class of adjuvants comprising an oily phase that is emulsified with an antigen-bearing aqueous phase. IFA consists of 90% purified light mineral oil combined with 10% mannide monooleate an emulsifier. IFA is formulated in equal volume with aqueous phase, containing antigen, to create a 1:1 water-in-oil emulsion that constitutes the vaccine. (A more potent form, Freund's Complete Adjuvant, additionally contains 0.5 mg heat killed Mycobacterium tuberculosis or butyricum per mL of oily phase, which significantly enhances immunopotency but which is too reactogenic for use in man.) IFA substantially increases humoral responses to particulate and soluble antigens in comparison with antigen given in aqueous phase alone. The principal mode of action is believed to result from a depot effect, wherein prolonged release of antigen from the emulsion in the injection site results in sustained stimulation of antibody production (Freund, J., 1956; McKinney, R. W. and Devenport F. M, 1961; Herbert, W. J., 1968). Additional potential mechanisms have also been identified, including facilitation of antigen dissemination (as emulsion) via the lymphatic system to distant sites and enhancement of monocyte infiltration to sites of emulsion deposition.

Inactivated influenza vaccine adjuvanted with IFA was tested in humans starting in the early 1950's. Promising initial immunopotency results led to large scale testing in the U.S. Armed Forces and in Great Britain (Hilleman, M. R., 1968; Davenport, F. M., 1968). It was shown that IFA significantly enhanced immunogenicity, providing a dose sparing effect while concurrently stimulating sustained antibody production relative to non-adjuvanted influenza vaccine. However, increased injection site reactions to the IFA adjuvanted vaccine were observed, particularly in early trials which used less pure adjuvant components. Injection site reactions observed with IFA ranged from inflammation, to granulomas, to sterile abscesses and cysts (Gupta, R. K., et al, 1993). Local reactions arose shortly after injection or presented after a period of time had elapsed following vaccine administration; with some reactions being detectable up to a year after injection (Stuart-Harris, C. H., 1957). Persistence of non-metabolizable mineral oil at the injection site is thought to be involved with sustained reactions. Removal of impurities from the mineral oil and mannide monooleate components, and administration intramuscularly, helped to substantially reduce local reactions in large follow-up studies. Thus, it was observed that the rate of cyst formation in recipients of IFA influenza vaccine was 3-23/10,000 (Davenport, F. M., 1961). Local reactogenicity with viral vaccines containing IFA was not limited to influenza vaccine; thus, in 8,497 individuals given IFA poliomyelitis vaccine, the combined rates of injection site tenderness, induration or nodule formation was 22/10,000 (Cutler, J. C., et al, 1963). Other than local injection site reactions, no other side effects are associated with IFA adjuvanted vaccines. A report that IFA was linked to oncogenicity in male Swiss mice has proved unfounded; elevated rates of cancer have not been observed in man in an extensive long term (35 year) follow up of 13,545 IFA-influenza vaccine recipients compared to 18,294 controls (Page, W. F., et al, 1993). This long term follow up study also identified that cases of hypersensitivity reported in some vaccinees was linked to penicillin contaminant in the viral vaccine preparation, and local cysts, which were linked to impurities in the mannide monooleate preparation used in the IFA. Despite the identification of factors responsible for reactogenicity and their reduction or removal from the vaccine components, mineral oil containing adjuvants have not been widely adopted for use in man (Gupta, R. K., et al, 1993).

The pressing need for adjuvanted influenza vaccines suggests that the risk/benefits associated with IFA should be seriously reevaluated. Evidence for the potential benefits for dose sparing, and improved immunogenicity and protection in the elderly by incorporating adjuvants in influenza vaccine formulations can be drawn from studies evaluating alum-based adjuvants and oil-in-water adjuvants, even though these adjuvants are typically not nearly so effective immunostimulants as IFA.

Aluminum salts, including aluminum hydroxide and aluminum phosphate, are effective at enhancing responses to toxoid antigens in man and have been assessed as adjuvant for influenza vaccines. A 1958-9 study in the U.K., found that aluminum phosphate failed to enhance antibody responses to inactivated influenza virus vaccine (Himmelweit, F., 1960). More recently, a clinical study with an alum-adjuvanted monovalent influenza whole virus vaccine showed that doses as low as 1.9 µg offered protective immunity compared to non-adjuvanted vaccine containing 15 µg HA per dose (Hehme, N. et al, 2004). However, in other studies alum has failed to provide any measurable benefit. Thus, immunization with two injections of A/H5N1 antigen in alum given at a 1 month interval provided no benefit over non-adjuvanted immunogen in a phase I/II clinical trial conducted in adults aged 18-49 years (Keital, W. A., et al., 2008). Similarly, a randomized double-blind study in 394 healthy adults found no enhancement of antibody titers in response to two injections of alum adjuvanted A/H5N1 vaccine in comparison with vaccine in saline (Bernstein, D. I., et al., 2008). The failure of alum to enhance responses in the healthy adults under 65 years of age in these studies sheds considerable doubt on the alum's capacity to be of significant benefit to the elderly.

MF59, an oil-in-water adjuvant approved for use in Europe has been compared to several non-adjuvanted licensed influenza vaccines in over 20 clinical trials. The oil in MF59 is squalene, which is metabolizable. The MF59-adjuvanted subunit vaccine, FLUAD is reportedly more immunogenic in the elderly than a conventional subunit vaccine (AGRIPAL) (Gasparini, R., et al, 2001) and an inactivated split influenza vaccine (VAXIGRIP) (Squarcione S., et al, 2003) and induced 1.1 to 1.3-fold higher antibody titers compared to conventional non-adjuvanted split influenza vaccines (Podda, A., 2001, Li, R., et al., 2008). Reactogenicity was reported to be greater in the FLUAD recipients, although not limiting, with higher rates of mild and transient local reactions being observed. The benefits of the vaccine were considered to outweigh the drawbacks, and FLUAD is approved for use in Europe. However, FLUAD has not exhibited enhanced efficacy in all patient populations. Thus, FLUAD reduced pneumonia related hospital admission rates by 50% in patients over 64 years of age relative to non-vaccinated controls (Puig-Barbera, J., 2004). However, no advantage was seen with FLUAD in terms of reported rates of influenza symptoms in heart transplant recipients on immunosuppressive regimens (Magnani, G., et al, 2005).

The potential health care benefits of enhancing the potency of influenza vaccine are well recognized and have stimulated considerable research in this field. Although limited improvements have been demonstrated for adjuvanted influenza vaccines formulated with alum and MF59, there clearly remains the need for improvement in this area. The present invention relates to adjuvanted influenza vaccines consisting of flu antigens formulated in a water-in-oil emulsion comprising naturally occurring oils and emulsifiers derived from vegetable sources. IFA, a well known water-in-oil adjuvant system, has already been demonstrated to significantly increase the immunopotency of influenza vaccine antigens. The influenza vaccines of the invention can be manufactured either point-of-use allowing pre-positioning of the adjuvant vehicle in the supply chain or in bulk by a robust, reproducible, and process.

Testing has been conducted with MF59 oil-in-water emulsion adjuvant (Chiron/Novartis) whereby it was demonstrated that MF59 modestly enhanced the immunogenicity of seasonal influenza trivalent subunit vaccine and was accompanied by an acceptable safety profile in the elderly. Mean antibody titers against the three viral strain-specific hemagglutinin components of the vaccine were higher in patients receiving MF59 adjuvanted vaccine, with mean serum antibody titer ratios of adjuvant versus non-adjuvant cohorts ranging from 1.1 to 1.3 fold, depending on the viral component against which the sera were assayed (Gasparini, R., et al, 2001). Even higher response ratios were associated with patients with pre-immunization titers≤40 in a different study (De Denato, S., et al, 1999). These studies reported higher rates of injection site reactions for patients vaccinated with the MF59 adjuvanted formulation than with standard vaccine, though the majority of such reactions were mild and the difference in reaction rates was not found to be significant relative to the reactogenicity of non-adjuvanted vaccine. The results of the clinical trials, summarized by Podda, A., 2001) were sufficiently favorable that the MF59 influenza vaccine (Fluad™) was granted approval in Europe. The experience with MF59 demonstrates that split virion vaccine can be formulated with adjuvant without adversely affecting performance as assessed by serological assays for anti-influenza antibody titers and standard safety parameters.

SUMMARY OF THE INVENTION

This invention involves prophylactic influenza vaccines comprising influenza vaccine antigens formulated as a nanoparticulate water-in-oil emulsion with an adjuvant vehicle derived from naturally occurring oils and emulsifiers. The invention is advantageous, in that it can be formulated by a batch manufacturing process (BMP) on a large scale adequate for prophylactic vaccines, or it can be formulated at the point of administration with oil adjuvant vehicle and influenza vaccine antigens as a miniemulsion by a point-of-use (POU) mixing method.

The vaccine of the invention, depending on the influenza antigens used in its formulation, should induce the production of immunoprotective antibodies against antigenically dissimilar virus strains and/or against additional less antigenic epitopes that cross react between viral strains to a much greater degree than is characteristic for antibodies induced by the standard, non-adjuvanted vaccine and should extend the period after immunization that immunoprotective titers remain elevated. The vaccine compositions comprise nanoparticulate water-in-oil emulsions. The aqueous phase of the emulsions comprises from about 25% to about 35% by weight of the composition and contains the influenza antigen or antigens. The oil phase of the emulsions comprises an adjuvant oil comprising squalene and squalane, a first emulsifier which is mannide monooleate or sorbitol monooleate and a second emulsifier selected from the group consisting of polyoxyl-40-hydrogenated castor oil, sorbitan monopalmitate, a polysorbate (e.g Tweens), Hypermer B239 or Hypermer B246. The nanoparticulate emulsions are formulated so that the median aqueous globule size is from about 0.3 μm to about 1 μm.

One example of the invention concerns a method for the point of use formulation of adjuvanted nanoparticulate water-in-oil emulsion vaccines. The method comprises preparing an aqueous solution of a proteinaceous antigen such as an influenza antigen, transferring a suitable amount of the aqueous solution to a sterile container containing a predetermined amount of the adjuvant oil, shaking the container so as to mix the contents to form a milky pre-emulsion, and transferring an aliquot of the milky pre-emulsion to a first sterile syringe. The first sterile syringe is connected to a sterile three-way stopcock to which a second sterile syringe is attached at a 90 degree angle to the first syringe. The emulsion is passed from one syringe to the other by manually depressing the plunger of each respective syringe in a serial fashion for a sufficient number of cycles so as to create an emulsion of the aqueous solution in the adjuvant oil wherein the median globule size is from about 0.3 μm to about 1 μm.

As a result of the enhanced immunogenicity, the inventive vaccines should enable a reduction in the quantity of antigen delivered per dose of vaccine, thereby extending antigen stocks to provide for the production of larger quantities of vaccine from the same quantity of antigen. This would be of particular benefit for both the alleviation of shortfalls in annual manufacture of vaccine as well as enabling an increase in the number of doses of vaccine in limited supply to counter newly emerging influenza strains, such as avian influenza and pandemic strains.

The "point of use" vaccine products permit pre-positioning of the adjuvant vehicle for local, as needed formulation with the then prevailing influenza strain viral antigens, and should result in significant supply chain and potential cost savings benefits to national governments planning pandemic flu preparedness. The adjuvant is suitable for combination with influenza vaccine preparations that target different strains of virus and thus, can be used with vaccines that are adjusted for viral specificity on an annual basis. An added benefit of the vaccines of the invention should be to increase influenza vaccine response rates in the elderly and otherwise immunocompromised subjects.

DESCRIPTION OF THE FIGURES

FIG. 1: Comparison of POU and BMP Vaccine Emulsions according to the invention (MAS-1). Mean globule size distribution D(v,0.5)±SEM of "point-of-use" emulsions of as little as 1.0 mL are within specification of ≤1 μm, and comparable to the emulsions produced by the bulk manufacturing process at 0.4, 2.0 and 10 L. Protein antigen (solid bars) up to at least 9.25 mg/mL in the aqueous phase has no effect on globule size distribution.

Figure 2:
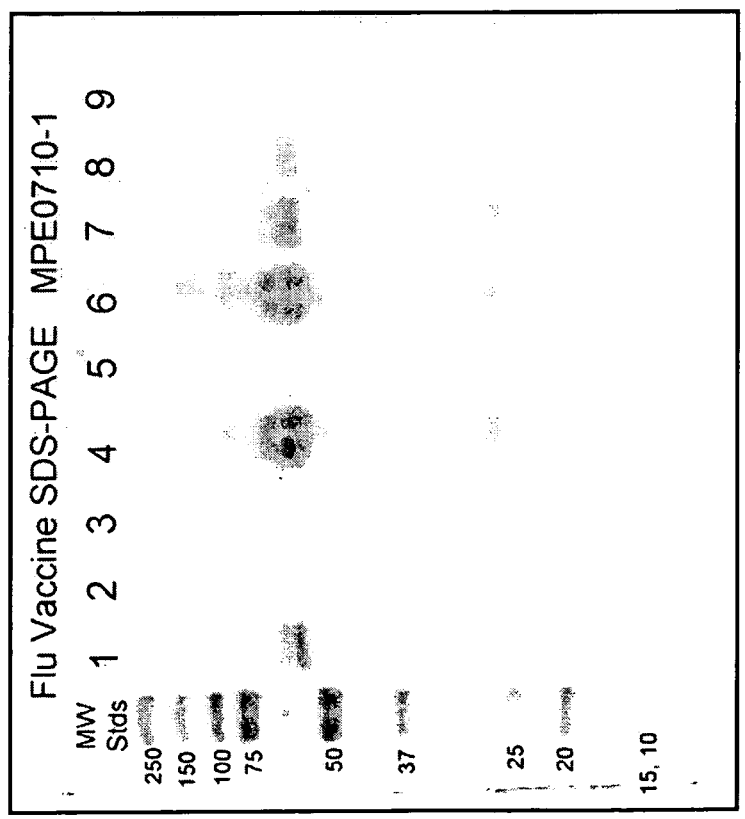

FIG. 2: SDS-PAGE of FLUZONE™ trivalent influenza vaccine, aqueous phase and extracted aqueous phase samples. Test Samples: FLUZONE™ (1) 15 µg/mL, (2) 5 µg/mL; (3) TIV filtrate; TIV concentrate (4) 1:3 dilution, (5) 1:27 dilution); TIV concentrate used in a vaccine according to the invention (MAS-1/TIV) (6) 1:3 dilution, (7) 1:9 dilution; MAS-1/TIV aqueous phase extract (8) 1:3 dilution, (9) 1:27 dilution. MW standards: Precision Plus Protein Standards, BioRad #161-0374: mol. Wt. 10, 15, 20, 25, 37, 50, 75, 100, 150, 250 KDa. using In Vitrogen Novex 10% Mini-Gel (#7102570-0877) with NuPAGE MOPS SDS running buffer (25 mL+475 mL $H_2O$).

FIG. 3A: Immunopharmacokinetics, Geometric mean HAI antibody titers to the viral antigen A/H1N1 in mice (n=6/grp) immunized subcutaneously on day 0 and day 28 with doses of H Ag formulated with MAS-1 (0.05, 0.15, 0.4, 1.3 and 4.0 μg) and control TIV (4.0 μg).

FIG. 3B: Immunopharmacokinetics, Geometric mean HAI antibody titers to the viral antigen A/H3N2 in mice (n=6/grp) immunized subcutaneously on day 0 and day 28 with doses of H Ag formulated with MAS-1 (0.05, 0.15, 0.4, 1.3 and 4.0 μg) and control TIV (4.0 μg).

FIG. 3C: Immunopharmacokinetics, Geometric mean HAI antibody titers to the viral antigen B/Malaysia in mice (n=6/grp) immunized subcutaneously on day 0 and day 28 with doses of H Ag formulated with MAS-1 (0.05, 0.15, 0.4, 1.3 and 4.0 μg) and control TIV (4.0 μg).

FIG. 3D: Dose Response Analysis, Day 56 Geometric Mean HAI titers to the A/H1N1, A/N3N2 and B/Malaysia viral antigens.

FIG. 4A: Immunopharmacokinetics, Geometric mean HAI antibody titers to the viral antigen A/H1N1 in rabbits (n=5/grp) immunized on day 0 and day 28 intramuscularly with doses of H Ag formulated with MAS-1 (1.67, 5.0 and 15 μg) and control TIV (15 μg).

FIG. 4B: Immunopharmacokinetics, Geometric mean HAI antibody titers to the viral antigen A/H3N2 in rabbits (n=5/grp) immunized on day 0 and day 28 intramuscularly with doses of H Ag formulated with MAS-1 (1.67, 5.0 and 15 μg) and control TIV (15 μg).

FIG. 4C: Immunopharmacokinetics, Geometric mean HAI antibody titers to the viral antigen B/Malaysia in rabbits (n=5/grp) immunized on day 0 and day 28 intramuscularly with doses of H Ag formulated with MAS-1 (1.67, 5.0 and 15 μg) and control TIV (15 μg).

DETAILED DESCRIPTION

In one example, the vaccines of the invention can be produced either "point-of use" or as a "bulk filled" final drug product.

As a "point-of-use" product, the vaccine is formulated as a nanoparticulate emulsion made by a simple, but robust and reproducible hand mixing procedure. This is illustrated by the globule size diameter 50% distribution results (D(v,0.5) for emulsions determined by laser light diffraction between multiple operators and their stability at room temperature. At T zero, globule size distribution for "point-of-use" emulsions prepared by 4 operators at the lower and upper mixing limits of the method were N=29; Mean D(v,0.5) ±SEM=0.44±0.03 μm and N=26; Mean D(v,0.5) ±SEM=0.66±0.03 μm, respectively. Globule size measurements at 2, 18-24 and 48 hours after preparation indicated that there was no significant change in this parameter over the two-day storage period.

"Bulk-filled" vaccine emulsion is manufactured aseptically and filled into single use containers such as vials or ampules. The mechanized, bulk fill process should typically produce emulsions with a mean globule size diameter of approximately 0.30 μm. Protein antigen up to at least 9.25 mg/mL in the aqueous phase has no effect on globule size distribution for emulsions made by either the point-of-use or the bulk fill method.

The vaccine emulsions have a low viscosity affording syringeability so that as little as 0.1 mL doses can be administered to patients with high precision and reproducibility.

The components of the oil adjuvant vehicle suitable for use in the invention, comprise a first sugar ester emulsifier such as mannide monooleate (MMO) or sorbitan monooleate, a second emulsifier such as a hydrogenated castor oil, for example, polyoxyl-40-hydrogenated castor oil (POCO), and naturally occurring and metabolizable oils, preferably squalene and squalane. The metabolizable oils typically comprise from about 85% to about 90% by weight of the oil, the first sugar ester emulsifier from about 6% to 15%, i.e., about 9% to about 12%, or about 10% or 11% by weight of the oil, and the second emulsifier from about 0.1%-1.1%, i.e., 0.2% to about 1%, 0.4 to about 0.8%, 0.5% to about 0.7%, or about 0.6% by weight of the oil. The metabolizable oil component may be 10%, 20%, 30%, 40%, 50%, 60%, 70%, 80% or 90% squalene, and 10%, 20%, 30%, 40%, 50%, 60%, 70%, 80% or 90% squalane by weight, but the concentration of these components may vary plus or minus 10% within this component. A suitable adjuvant vehicle for use in the invention is MAS-1, which is comprised of naturally occurring and metabolizable components derived from vegetable sources, and is commercially available from Mercia Pharma, Inc, Scarsdale, NY (www-.merciapharma.com). Point-of-use (POU) vaccines may be produced with these adjuvant oils using a robust and reproducible hand-mixing method described herein.

The components of the oil vehicle, including their starting materials, which may be derived from either animal or vegetable sources, or combinations thereof, are all commercially available from multiple sources. Suitable sugar esters as the first emulsifier in addition to MMO include polysorbates, particularly sorbitan monooleate. In addition to POCO as the second emulsifier sorbitan esters, such as sorbitan monopalmitate, polysorbates, such as the Tweens family of emulsifiers, and Hypermers B239 and B246 may be useful.

The nanoparticulate vaccine emulsions of the invention typically contain from about 65% by weight to about 75% by weight of the adjuvant oil vehicle, but may also contain about 10%, 20%, 30%, 40%, 50%, 60%, 70%, 80% or 90% by weight of the adjuvant oil vehicle. The nanoparticulate vaccine emulsions of the invention typically contain from about 25% to about 35% by weight of an aqueous phase containing the protein antigen, but may also contain from about 10%, 20%, 30%, 40%, 50%, 60%, 70%, 80%, or 90% by weight of an aqueous phase containing the protein antigen. In certain embodiments of the invention the aqueous phase comprises from about 27% to about 33% by weight of the vaccine emulsion.

The water-in-oil vaccine emulsions used in the invention should be formulated so that the aqueous globules in the emulsion carrying the antigen have median diameters less than 1 micron with median diameters in the range from about 100 nanometers to about 1 micron, and typically with an average diameter of about 300 nanometers. It is further contemplated that the aqueous globules may be 50 nanometers, 100 nanometers, 150 nanometers, 200 nanometers, 250 nanometers, 300 nanometers, 350 nanometers, 400 nanometers, 450 nanometers, 500 nanometers, 550 nanometers, 600 nanometers, 650 nanometers, 700 nanometers, 750 nanometers, 800 nanometers, 850 nanometers, 900 nanometers, or 950 nanometers. The oil components of the adjuvant are preferably naturally occurring biological oils that are metabolizable, unlike the mineral oil that comprises the oil phase of the well known Freund's adjuvants (both incomplete and complete formulations).

The vaccine emulsions of the invention should tolerate high concentrations of antigen, such as from 0.1 mg/mL to 20 mg/mL, i.e, 1 mg/mL, 5 mg/mL, 7 mg/mL, 9 mg/mL, 10 mg/mL, 11 mg/mL, 13 mg/mL, 15 mg/mL, 20 mg/mL, or up to at least 10 mg/mL and should be compatible with commonly used protein solubilizers (e.g., 4M urea, 30% DMSO). Unlike IFA emulsions, they should be compatible with aqueous phases having a wide range of pH, i.e., from about 2-9, 3-8, 4-6, i.e., about 5, and unaffected over a wide range salt concentrations. Unlike IFA emulsions (>1,500 cP), the vaccine emulsions of the invention should have a low viscosity (<100 cP) as free flowing emulsions permitting high precision low volume (0.1 mL) dosing. The physico-chemical characteristics of the vaccine emulsions of the invention should have a median distribution of globule size diameter of (D(v,0.5)) less than or equal to 1.0 µm, and be unaffected by high concentrations of protein in the aqueous phase (FIG. 1).

At T zero, D(v,0.5) µm±SEM for POU vaccine emulsions prepared by four different operators at the lower and upper mixing limits of the method were; 0.44±0.30 (n=29) and 0.66±0.03 (n=26), respectively. D(v,0.5) after 2, 24 and 48 hours at ambient temperature indicated no significant change. At release, BMP vaccine emulsions should have a D,(v0.5) of 0.3 µm with an end of shelf life D,(v0.5) of ≤1 µm after 3 years at 2-8° C. without any loss in immunopotency in vivo (by contrast D(v,0.5) of IFA is 3-10 μm a T zero).

The invention is further described in the following examples. The examples are merely illustrative and do not in any way limit the scope of the invention as described and claimed.

EXAMPLE 1

TIV Vaccines: In one example of the invention the vaccines are comprised of standard TIV antigens derived from egg or cell cultures located in the aqueous phase, formulated as a 30:70 (w/w/) water-in-oil (w/o) nanoparticulate emulsion with MAS-1 having a median globule size diameter D(v,0.5) of 0.30 μm. A suitable adjuvant vehicle for use in the invention is MAS-1.

Formulation of TIV influenza vaccine: FLUZONE™ TIV, was obtained from Sanofi Pasteur, as the source of H antigen (Ag) for these studies. FLUZONE™ contains 30 μg/mL of each H antigen, and yields 9 μg/mL of each H antigen formulated in a 30:70 emulsion with MAS-1 adjuvant. FLUZONE™ TIV was concentrated up to 10-fold using Amicon Ultra 15 centrifugational concentrators (cut-off: 10,000 kd). During concentration of TIV approximately 50% of total protein determined by Lowry assay is recovered in the concentrate. Approx. 40% of total protein passes through the filters into the filtrate, and 12% is adsorbed to the ultrafilters (Table 1). TIV protein recovery was reproducible between batches. Total protein analyses of the aqueous phase by Lowry confirmed batch-to-batch consistency across the range of H Ag concentrations, with protein content of the aqueous phase varying ≤2.5% and 3.5% for FLUZONE™ between batches (Table 2).

TABLE 1

Recovery and Mass Balance of TIV protein during centrifugal concentration

| Aqueous Phase Test Sample | Total Protein (μg) Batch 1 | Total Protein (μg) Batch 2 |
|---|---|---|
| Fluzone | 12,020 | 12,440 |
| Concentrate | 5,893 (49.0%) | 5,928 (47.7%) |
| filtrate | 4,662 (38.8%) | 5,130 (41.2%) |
| Balance | 12.2% | 11.1% |

Although total protein was lost, H antigen was not lost during the concentration process. Total H antigen by single radial immunodiffusion (SRID) test comprises 14-15% of the total protein measured by Lowry (against BSA standard) in FLUZONE™, and 30-31% of the total protein in the vaccine emulsion formulations (Table 2). The validated SRID assay is used for batch release of approved influenza vaccines. We established the SRID assay in our laboratory, using the WHO methods and reference antisera and antigens. By SRID, all three H antigens were retained in the concentrate with no loss into the filtrate. These results were confirmed by SDS-PAGE run on samples of concentrate and filtrate (FIG. 2).

TABLE 2

Content and reproducibility of H antigen and total protein in MAS-1/TIV

| Immunogen For Group | Total (μg/mL) H Ag[1] | Protein (μg/mL) by Lowry[2] for Batch 1 | % [H Ag]/ [SRID] for Batch 1 | Protein (μg/mL) by Lowry[2] for Batch 2 | % [H Ag]/ [SRID] for Batch 2 | % (Batch-1/ Batch-2) |
|---|---|---|---|---|---|---|
| 1 (Fluzone) | 90.0 | 601 | 15% | 622 | 14% | −3.49% |
| 2 | 150 | 496 | 30% | 499 | 30% | −0.60% |
| 3 | 50 | 165 | 30% | 166 | 30% | −0.61% |
| 4 | 50 | 159 | 31% | 163 | 31% | −2.52% |
| 5 | 150 | 496 | 30% | 499 | 30% | −0.60% |
| 6 | 16.7 | 55 | 30% | 56 | 30% | −1.82% |
| 7 | 50 | 159 | 31% | 163 | 31% | −2.52% |
| 8 | 5.7 | 18.3 | 31% | 18.7 | 30% | −2.19% |
| 9 (Placebo) | 0 | 0 | NA | 0 | NA | NA |

[1]Total H Ag concentration from Fluzone specification

[2]Total protein (BSA equivalents) measured by Lowry against BSA standard;

NA Not applicable

EXAMPLE 2

POU Mixing Procedure Parameters: The range of mixing rate and mixing cycles optimal for making water-in-oil miniemulsion nanoparticulate vaccine emulsions according to the invention were established using an aqueous phase comprising phosphate buffered saline (PBS), pH 7.2 and MAS-1 oily vehicle in a 30:70 (w/w) ratio made using the POU mixing procedure. A range of mixing rates and mixing cycles were evaluated at syringe sizes from 1.0 to 5.0 mL and emulsion volumes ranging from 1.0 to 3.0 mL. Samples were analyzed immediately after preparation (T-zero) and at select times after storage at ambient conditions for up to 1 week. The data are presented in Table 3.

TABLE 3

Physico-chemical characteristics of POU 30:70 (w/w) MAS-1 Vaccine emulsions

| Replicates (N)* | Mix Cycles | Mixing Duration (sec) | Syringe Size/ emulsion vol (mL) | Globule size diam, D(v, 0.5) Mean (SD) μm | | | | |
|---|---|---|---|---|---|---|---|---|
| | | | | T-zero | 4-6 hr | 24 hr | 48 hr | 1 week |
| 8 | 40 | No Constraint | 1/1 | 7.68 (10.2) | 11.37 (14.6) | 1.58 | nr | nr |
| 3 | 50 | No Constraint | 1/1 | 1.46 (0.62) | 2.04 | nr | nr | nr |
| 3 | 60 | No Constraint | 1/1 | 12.00 (17.76) | nr | 14.29 (18.00) | nr | nr |
| 6 | 75 | No Constraint | 1/1 | 1.16 (0.32) | 1.40 | nr | nr | nr |
| 1 | 100 | No Constraint | 1/1 | 0.62 | nr | 0.70 | nr | nr |
| 11 | 125 | No Constraint | 1/1 | 0.64 (0.20) | nr | 0.40 | nr | nr |
| 6 | 125 | 90 | 1/1 | 0.33 (0.04) | nr | 0.36 | 0.44 | 0.40 (0.11) |
| 20 | 125 | 100 | 1/1 | 0.47 (0.20) | 0.31 | 0.43 (0.11) | 0.48 (0.01) | 0.53 (0.33) |
| 6 | 125 | 110 | 1/1 | 0.74 (0.07) | nr | nr | nr | nr |
| 17 | 125 | 120 | 1/1 | 0.60 (0.16) | 0.57 (0.13) | 0.70 (0.16) | 0.83 (0.07) | 0.82 (0.19) |
| 2 | 125 | 150 | 1/1 | nr | nr | 0.91 (0.07) | nr | 0.99 |
| 3 | 125 | 90 | 3/2 | 0.31 (0.01) | 0.30 | 0.31 | 0.30 | nr |
| 1 | 125 | 180 | 3/2 | 0.75 | nr | nr | nr | nr |
| 1 | 125 | 135 | 5/5 | 0.30 | nr | 0.31 | nr | nr |

Note:
nr = not reported;
*Replicates (N) refers to the number of emulsions produced under the stated condition The combined (N=52) results for physico-chemical characteristics of 1 and 2 mL POU MAS-1 vaccine emulsions prepared with 1 and 3 mL syringes, respectively, made by 125 cycles in the range 90 to 120 seconds presented in Table 4.

TABLE 4

Physico-chemical characteristics of POU 30:70 (w/w) MAS-1 Vaccine emulsions

| Characteristics | T zero | Storage at Ambient Temperature | | | |
|---|---|---|---|---|---|
| | | 4-6 hr | 24 hr | 48 hr | 1 wk |
| Viscosity cP | 86 | nr | nr | nr | nr |
| Globule size D(v0.5) Mean (SD) μm | 0.52 (0.2) | 0.44 (0.17) | 0.47 (0.17) | 0.56 (0.22) | 0.61 (0.27) |
| Appearance score | 0 (0) | 0 | 0 | 0 | nr |

Key to Appearance Scores

The samples, contained in clear glass vials, are visually examined under defined lighting for the presence of aqueous droplets collecting at the bottom of the emulsion. The method gives a macroscopic measure of the quality of the emulsion.

| 0 | No aqueous droplets were observed |
|---|---|
| 1-3 | Increasing amounts (quantity and size) of aqueous droplets were observed |
| 4 | An aqueous pool was observed |
| 5 | An aqueous layer was observed |
| 6 | a complete phase separation was observed |

The POU method produces reproducible, robust, and stable MAS-1 vaccine emulsions when mixed for 125 cycles within 90-120 seconds at the 1 to 2 mL. Scale and 90-150 seconds at the 5 mL scale.

EXAMPLE 3

Immunopotency Enhancement in Mice of MAS-1/TIV: The objective of this dose ranging study was to evaluate the immunopotency and dose sparing benefits of MAS-1 adjuvant on TIV in mice. The study was designed to generate data on primary and secondary response parameters, including antibody titers, response kinetics, isotype and specificity following immunization with the adjuvanted vaccine of the invention compared to standard TIV vaccine. General well-being of the animals was monitored throughout the study period.

Test formulations: Prior to emulsification with MAS-1 vehicle, H antigen from TIV concentrate was diluted with PBS to yield aqueous phases with the correct concentrations of H antigen. H antigen concentrations were calculated from the H antigen content of the starting material (FLUZONE™) and the volume following concentration by centrifugal ultra-filtration. The aqueous phase protein contents were confirmed by Modified Lowry Assay (Pierce Chemical Co.). The TIV aqueous phase preparations were readily emulsified in MAS-1 oil phase vehicle using the POU mixing procedure.

The vaccine emulsions were broken to extract the aqueous phase and oil phases. SDS-PAGE analysis of antigen-bearing aqueous phase extracted from the emulsion demonstrated that the antigens are compatible with the MAS-1 adjuvant. Protein mobility and band numbers were the same between aqueous phase and extracted aqueous phase.

Study outline: The study was a seven-arm, placebo controlled study at doses/H antigen (A/H1N1; A/H3N2; and, B) of 4.0 μg as TIV (+ control); MAS-1 placebo (− control), and 0.05 to 4.0 μg of TIV formulated as a nanoparticulate emulsion with MAS-1 according to the invention. BALB/c mice (female, 8-12 weeks old at start of study, 6 per group) were immunized with 0.1 mL test articles subcutaneously (dorsal, base of neck) on days 0 and 28. Blood samples were taken on days 0, 14, 28, 42, and 56. Sera were prepared and stored at −20° C. until assay. The formulations were prepared from clinical grade 2007/08 season TIV (FLUZONE™). FLUZONE™ was concentrated 10-fold to 452 μg/mL total H antigen aqueous phase. The vaccine and placebo emulsions were prepared by the POU method. The aqueous phase protein content for the vaccine preparations were verified by Modified Lowry and SDS-PAGE.

General Safety: None of the mice showed any signs of distress or ill health over the course of the study at any of the doses tested indicating that the formulations were safe and well tolerated.

Immunopotency and enhancement: The hemagglutination inhibition (HAI) titers against each of the three viral strains used in the 2007/08 TIV (A/Solomon Islands/3/2006 (H1N1); A/Wisconsin/67/2005 (H3N2); B/Malaysia/2506/200) were measured using the WHO assay protocol and reference standards. Testing was performed blinded to group assignment. Group geometric mean HAI titers at days 42 and 56 for the three influenza viral antigens and the dose adjusted enhancement of the immune response in MAS-1/TIV vaccine according to the invention for each antigen relative to TIV (Group 1) are presented in Table 5. MAS-I significantly enhanced the immunopotency of TIV against three component viral strains at both time points, particularly on day 56. At the matched 4 μg dose, MAS-1 enhanced the day 56 responses by 9 fold for A/H1N1 virus, 11.3 fold for A/H3N2 virus, and 6.3 fold for B virus. Higher HAI titers were observed at day 56 even at 0.15 μg/H antigen in the adjuvanted vaccine compared with 4 μg/H antigen in standard TIV group 1, with dose adjusted enhancement of 48-fold for A/H1N1, 85-fold for A/H3N2, and 23-fold for B/Malaysia. Overall, dose-adjusted enhancement of TIV in MAS-1/TIV at day 56 compared to standard TIV was 22 fold for A/H1N1, 26-fold for A/H3N2, and 9-fold for B/Malaysia.

TABLE 5

Geometric mean HAI titers of test groups and dose-adjusted enhancement of HAI titers relative to Fluzone positive control (group 1).

| | | | Titer | | | | | |
|---|---|---|---|---|---|---|---|---|
| | | | A/H1N1 | | A/H3N2 | | B | |
| | | | Bleed day | | | | | |
| Group | Treatment | | 42 | 56 | 42 | 56 | 42 | 56 |
| 1 | TIV 4 μg | Geo. Mean | 1,280 | 905 | 1,611 | 905 | 285 | 226 |
| | | (+) Control | — | — | — | — | — | — |
| 2 | MAS-1/TIV 4 μg | Geo. Mean | 5,747 | 8,127 | 25,803 | 10,240 | 905 | 1,437 |
| | | Enhanced | 4.5 | 9.0 | 16.0 | 11.3 | 3.2 | 6.3 |
| 3 | MAS-1/TIV 1.3 μg | Geo. Mean | 2,874 | 4,561 | 905 | 2,032 | 137 | 359 |
| | | Enhanced | 6.8 | 15.2 | 1.7 | 6.8 | 1.4 | 4.8 |
| 4 | MAS-1/TIV 0.4 μg | Geo. Mean | 1,016 | 1,613 | 118 | 149 | 9 | 16 |
| | | Enhanced | 7.2 | 16.2 | 0.7 | 1.5 | 0.3 | 0.6 |

TABLE 5-continued

Geometric mean HAI titers of test groups and dose-adjusted enhancement of HAI titers relative to Fluzone positive control (group 1).

| | | | Titer | | | | | |
|---|---|---|---|---|---|---|---|---|
| | | | A/H1N1 | | A/H3N2 | | B | |
| | | | | | Bleed day | | | |
| Group | Treatment | | 42 | 56 | 42 | 56 | 42 | 56 |
| 5 | MAS-1/TIV 0.15 µg | Geo. Mean | 806 | 1,613 | 1.016 | 2,874 | 20 | 194 |
| | | Enhanced | 16.8 | 47.5 | 16.8 | 84.7 | 1.9 | 22.9 |
| 6 | MAS-1/TIV 0.05 µg | Geo. Mean | 5 | 7 | 3 | 3 | 1 | 1 |
| | | Enhanced | 0.03 | 0.6 | 0.1 | 0.3 | 0.3 | 0.4 |
| 7 | MAS-1 placebo | Geo. Mean | 1 | 1 | 1 | 1 | 1 | 1 |
| | | (−) Control | — | — | — | — | — | — |
| Combo | 0.15-4.0 | Enhanced | 8.8 | 22.0 | 8.8 | 26.1 | 1.7 | 8.7 |

Note:
Enhancement = (test group mean/group 1 mean) × (H Ag dose of group 1/H Ag dose of test group)

Figure 3A:
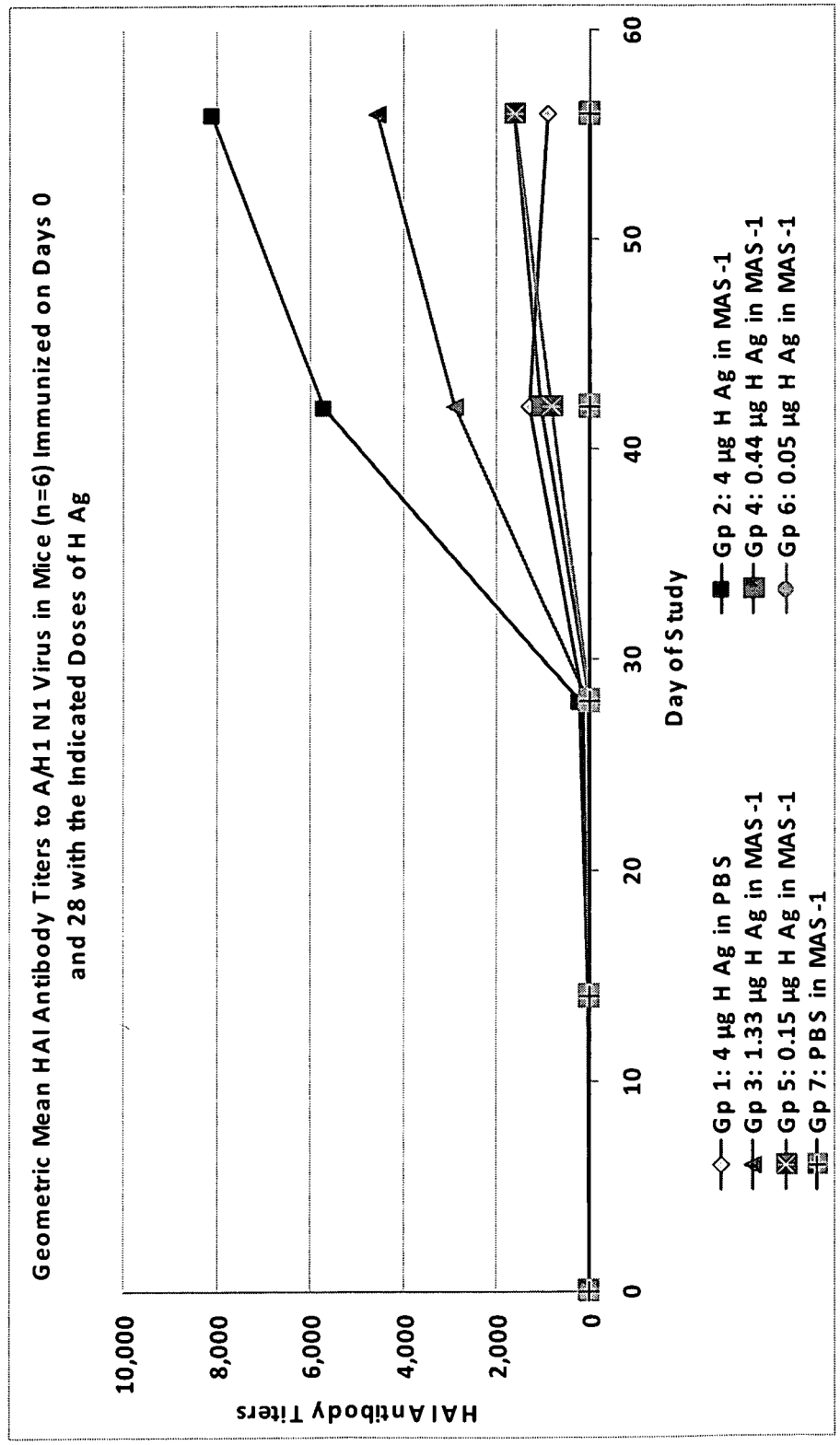
Figure 3C:
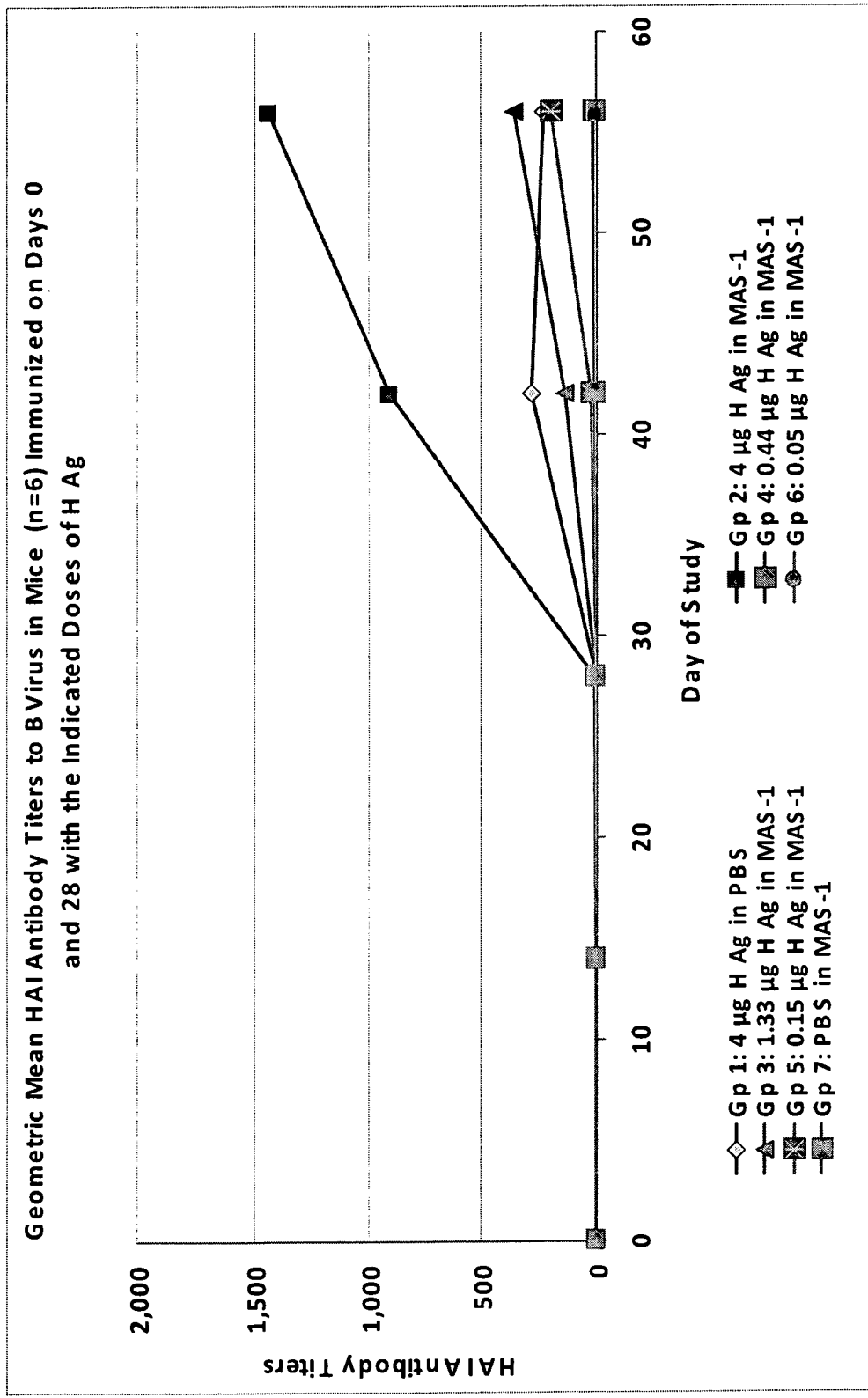
Figure 3D:
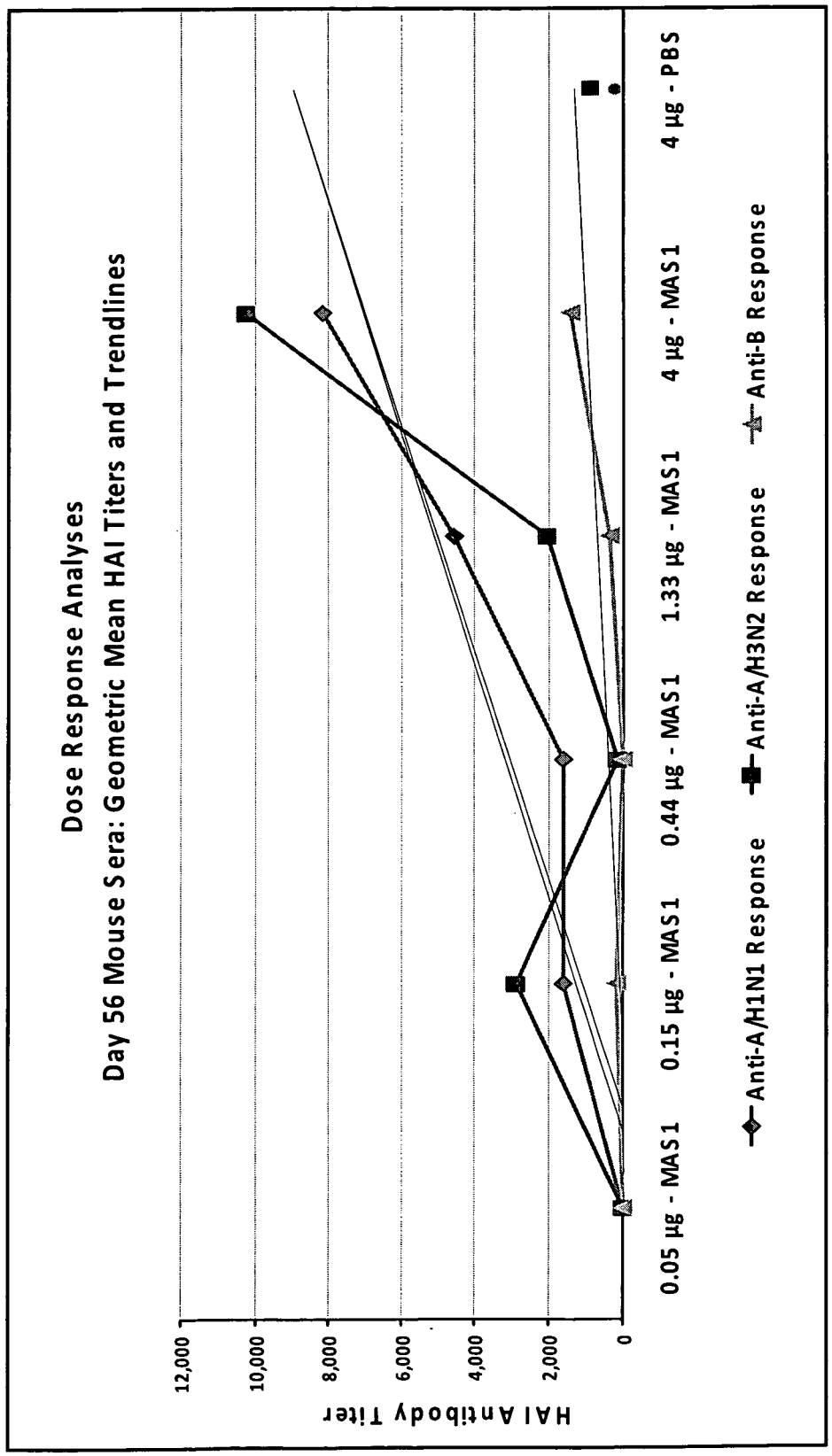

Immunopharmacokinetics: Antibody response kinetics were similar for each of the three component strains (FIGS. 3.A-C). Predictably in naïve mice, relatively low HAI responses were seen following injection 1 in all responding groups, while enhanced responses followed injection 2, indicative of immune priming by the first dose. By day, 56 HAI titers with TIV were beginning to fall off, whereas for the MAS-1 adjuvanted vaccine, HAI titers were still rising, indicating that immunization with the adjuvanted vaccine of the invention extends the period for providing protection over standard TIV. The relative HAI titers for B virus elicited by TIV were significantly lower than for A virus strains, whereas, in the adjuvanted vaccine, B virus titers were comparable to A virus titers in standard TIV.

Dose response: The dose-related response of HAI titers for each of the three viral antigens, A/H1N1, A/H3N2, and B virus elicited by the adjuvanted formulations of the invention is further illustrated by the data for day 56 presented in FIG. 3D. These data show that 0.15 to 4 µg/H antigen in MAS-1 is in a titrating range, and indicate that the mouse model should be suitable as an in vivo immunopotency release and stability indicating assay. Precision will be attained by using 10 up to 25 animals per group with release specifications to be made relative to TIV control.

EXAMPLE 4

Evaluation of Efficacy and Safety in Rabbits

Study outline: A dose ranging, placebo controlled 9 arm (N=5/group) study was performed in rabbits to evaluate enhancement of immunopotency, dose sparing potential, and duration of immunoprotective response versus standard TIV at doses and route of administration anticipated in humans. Additionally, the study incorporated both general safety and a formal evaluation of toxicology to evaluate injection site tolerance and systemic safety by necropsy and histopathology on a panel of organs. The study encompassed a range of variables, including: MAS-1 vs. no adjuvant (FLUZONE™), dose of H antigen in MAS-1 (0, 0.56, 1.67, 5.0, and 15.0 µg/H antigen), injection volume (0.1 and 0.3 mL), and formulation strategy (emulsified to strength or dilution of vaccine emulsion to H antigen strength with placebo emulsion). Animals were immunized intramuscularly on days 0 and 28. Blood samples were taken on day 0 and at 2 weekly intervals through day 84. Sera was prepared from the blood samples and stored at −20° C. until assay. Animals were sacrificed on day 84, necropsied and organs collected for gross evaluation and histopathology in compliance with GLP. Formulations were prepared from clinical grade 2007/08 season TIV (FLUZONE™), and vaccine and MAS-1 placebo emulsions were prepared by the POU method. The aqueous phase protein content for vaccine preparations was verified by Modified Lowry and SDS-PAGE.

Figure 4A:
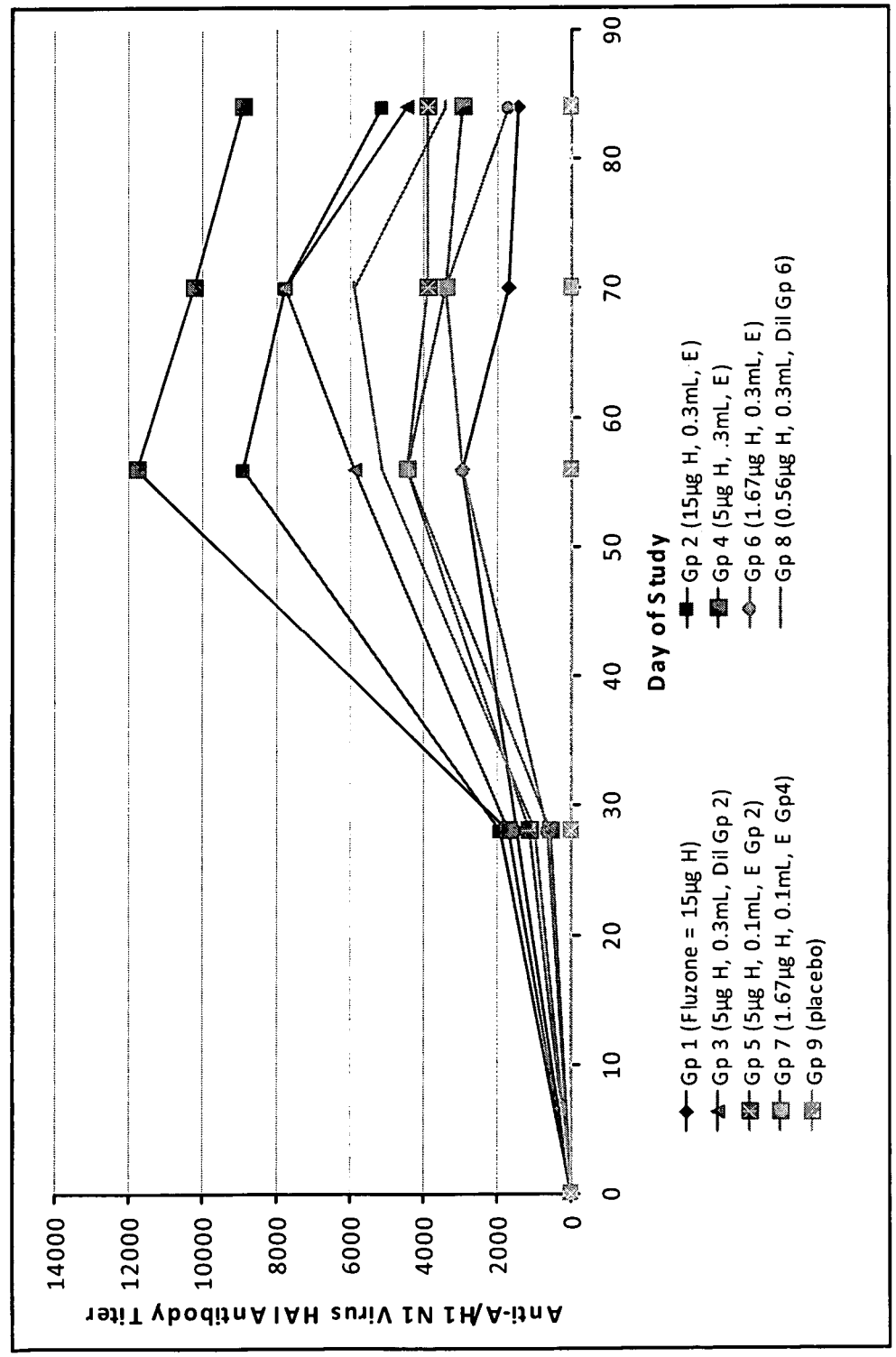
Figure 4B:
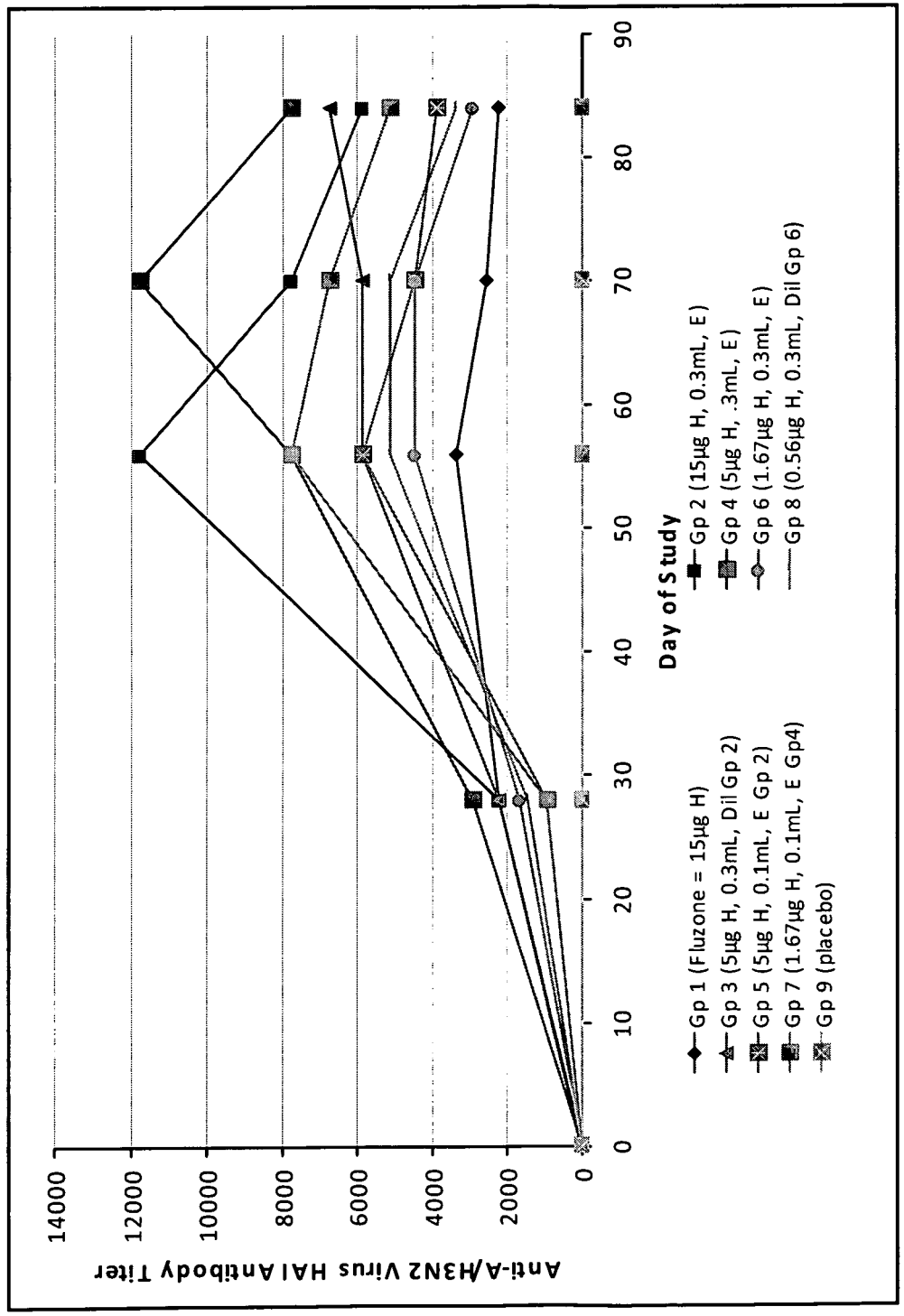
Figure 4C:
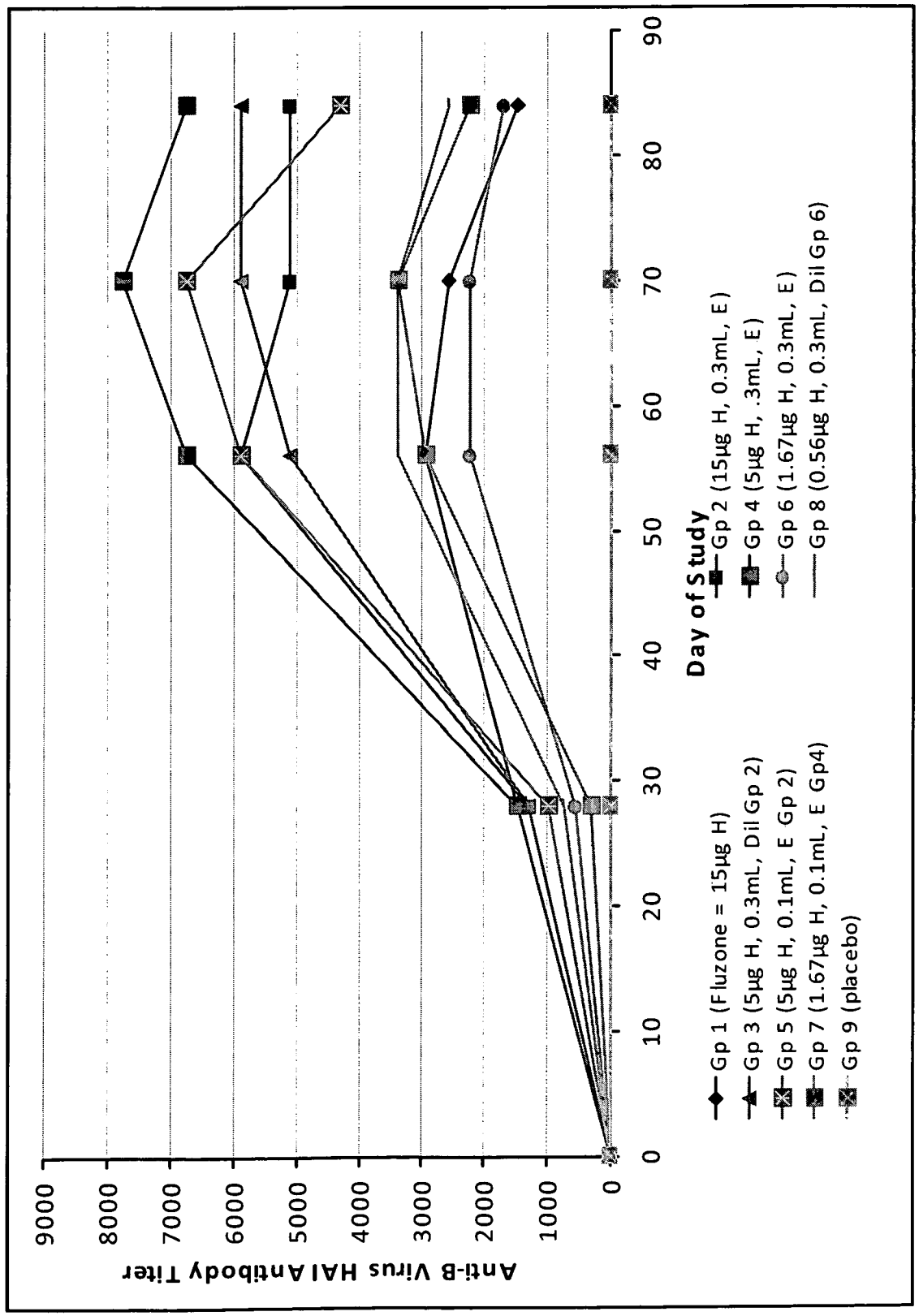

Immunopotency and enhancement: HAI titers were measured against the three viral strains present in the 2007/08 TIV, and against the three antigenically dissimilar strains in the 2008/09 TIV to evaluate cross-immunoprotection. Testing was performed blinded to group assignment. Peak HAI titers for the three 2007/08 and 2008/09 season virus strains and dose adjusted enhancement of HAI titers by MAS-1 for each antigen are presented in Tables 6A and B, respectively. The immunopharmacokinetics of the immune response induced by TIV and MAS-1/TIV after IM immunization are shown in FIGS. 4A, B and C. MAS-1 significantly enhanced the immunopotency of TIV antigens at all doses against 2007/08 viral strains compared to TIV (positive control—group 1). At the matched 15 µg dose, MAS-1 enhanced peak responses 3-fold for A/H1N1, 3.5-fold for A/H3N2, and 2-fold for B viruses. Even at 0.56 µg/H antigen, MAS-1 enhanced HAI titers compared with 15 µg/H antigen in standard TIV by 2-fold for A/H1N1, 1.7-fold for A/H3N2, and 1.3-fold for B viruses, with dose adjusted enhancement of 54-fold for A/H1N1, 47-fold for A/H3N2, and 35-fold for B/Malaysia. ANOVA comparisons between HAI titers for each of groups 3, 4 and 5, at 5 µg H antigen, and groups 6 and 7 at 1.67 µg/H antigen were statistically equivalent, indicating that differences in dose volume of 0.1 vs. 0.3 mL, or in formulation strategy (direct emulsion vs. diluted emulsion) were equivalent. Group 9, comprising negative controls injected with placebo MAS-1 emulsion, produced no detectable anti-influenza antibodies (Table 6A).

TABLE 6A

Peak Geometric mean HAI titers and dose adjusted enhancement of MAS-1/TIV Against 2007/08 Season Virus Strains

| 2007/08 Season Grp | Dose (μg) | Vol (mL) | A/H1N1 Solomon Islands/3/2006 | | | A/H3N2 Wisconsin/67/2005 | | | B Malaysia/2506/2004 | | |
|---|---|---|---|---|---|---|---|---|---|---|---|
| | | | Titer | Enhanc | p value | Titer | Enhanc | p value | Titer | Enhanc | p value |
| 1 | 15 | 0.5 | 2941 | — | — | 3378 | — | — | 2941 | — | — |
| 2[a] | 15 | 0.3 | 8914 | 3.0 | 0.001 | 11763 | 3.5 | 0.015 | 5881 | 2.0 | 0.059 |
| 3[b] | 5 | 0.3 | 7760 | 7.9 | 0.005 | 7760 | 6.9 | 0.086 | 5881 | 6.0 | 0.089 |
| 4[a] | 5 | 0.3 | 11763 | 12.0 | 0.018 | 11763 | 10.4 | 0.004 | 8914 | 9.1 | 0.002 |
| 5[c] | 5 | 0.1 | 4457 | 4.5 | 0.207 | 6756 | 6.0 | 0.034 | 6756 | 6.9 | 0.031 |
| 6[a] | 1.67 | 0.3 | 3881 | 11.9 | 0.326 | 4457 | 11.9 | 0.242 | 2561 | 7.8 | 0.620 |
| 7[a] | 1.67 | 0.1 | 4458 | 13.6 | 0.167 | 8914 | 23.7 | 0.203 | 3379 | 10.3 | 0.658 |
| 8[b] | 0.56 | 0.3 | 5882 | 53.6 | 0.030 | 5881 | 46.6 | 0.066 | 3882 | 35.4 | 0.460 |
| 9 | 0 | 0.3 | 0 | — | — | 0 | — | — | 0 | — | — |
| Overall | — | — | — | 15.21 | — | — | 15.57 | — | — | 11.07 | |

[a]Emulsified directly to the indicated concentration of H antigen.
[b]Emulsion prepared at strength for Group 2 was diluted 1:3 with placebo emulsion
[c]Same emulsion as that used for Group 2.
Enhancement over TIV = (test group mean/group 1 mean) × (H Ag dose of group 1/H Ag dose of test group)

EXAMPLE 5

Dose response: The dose response for the adjuvanted vaccine seen in mice appeared to be in the linear range. By contrast, the dose response of HAI titers for each of the three viral antigens, A/H1N1, A/H3N2, and B virus elicited after IM immunization in rabbits indicate that the lowest dose tested, 0.56 μg/H antigen, in MAS-1/TIV is close to the plateau response above the dose titration range—lower doses were not evaluated.

Cross-immunoprotection against 2008/09 Season Strains: Immunization with a vaccine according to the invention (MAS-1/TIV, using 2007/2008 TIV) was significantly more cross protective than standard TIV with HAI titers against 2008/09 TIV strains. At the 5 μg/H antigen dose all three MAS-1/TIV preparations were statistically equivalent by ANOVA, and enhanced on average 4.1-fold for A/H5N1, 3.4-fold for A/H1N1, and 2.4-fold for B viruses. The mean dose adjusted enhancement at 5 μg/H antigen was 12-fold for A/H1N1, 10-fold for A/H3N2, and 7-fold for B/Florida (Table 6B).

TABLE 6B

Day 56 Geometric mean HAI titers and dose adjusted enhancement of MAS-1/TIV Against 2008/09 Season Virus Strains

| 2007/08 Season Grp | Dose (μg) | Vol (mL) | A/H1N1 Brisbane/59/2007 | | | A/H3N2 Brisbane/10/2007 | | | B Florida/4/2006 | | |
|---|---|---|---|---|---|---|---|---|---|---|---|
| | | | Titer | Enhanc | p value | Titer | Enhanc | p value | Titer | Enhanc | p value |
| 1 | 15 | 0.5 | 320 | — | — | 320 | — | — | 279 | — | — |
| 2 | 15 | 0.3 | 1280 | 4.0 | 0.011 | 844 | 2.6 | 0.023 | 557 | 2.0 | 0.059 |
| 3 | 5 | 0.3 | 1470 | 13.8 | 0.010 | 1114 | 10.4 | 0.032 | 970 | 10.4 | 0.089 |
| 4 | 5 | 0.3 | 1470 | 13.8 | 0.002 | 1470 | 13.8 | 0.002 | 422 | 4.5 | 0.002 |
| 5 | 5 | 0.1 | 970 | 9.1 | 0.069 | 640 | 6.0 | 0.006 | 640 | 6.9 | 0.031 |
| Overall | 5-15 | — | — | 10.2 | — | — | 8.2 | — | — | 6.0 | |

Enhancement over TIV = (test group mean/group 1 mean) × (H Ag dose of group 1/H Ag dose of test group)
Student's T test in each case is compared to group 1 Fluzone positive control Immunopharmacokinetics: Antibody response kinetics were similar for each of the three component strains, as shown in FIGS. 4A, B, and C. MAS-1 enhanced titers remained elevated throughout days 56, 70, and 84 for all 3 viral strains, indicating that the adjuvanted vaccine of the invention administered by IM vaccination extends the period for maintaining protective HAI titers over those induced by the standard 15 µg/H antigen dose of FLUZONE™.

EXAMPLE 6

Safety/Toxicology Evaluations: The scope of the rabbit immunopharmacology included: observations of animal general well-being during the in vivo phase, and formal evaluations of safety and toxicology, including animal weights, necropsy, visual inspection and organ weights under veterinary supervision, and histopathology assessments of the 20 selected organs in Table 7 from Groups 1 (FLUZONE™ 15 µg), Group 2 (MAS-1/TIV 15 µg), and Group 9 (MAS-1 placebo), respectively; were performed in compliance with GLP. In addition, all injection sites were examined post mortem by visual and histological assessments on all rabbits.

TABLE 7

Tissues collected at necropsy for histopathology from each rabbit in Groups 1, 2 and 9.

| Tissue Collected | Sample Type |
| --- | --- |
| Heart, Spleen, Adrenal, Ovary, Popliteal lymph node, Mandibular lymph node, Brain | Whole |
| Kidney, Liver, Lung, Pancreas, Aorta, Stomach, Duodenum, Jejunum, Ileum, Cecum, Colon, Esophagus, Trachea | Section |

General Safety: FLUZONE™ TIV and all MAS-1/TIV formulations appeared safe and well tolerated during the in vivo phase of the study assessed by independent observations made by animal welfare personnel. No animals at any adjuvanted vaccine dose or FLUZONE™ showed signs of ill health at any point during the study. No statistically significant differences in body weights taken on day 72 were observed between the adjuvanted vaccine Groups 2-8 or MAS-1 placebo Group 9, or FLUZONE™ Group 1.

Necropsy: All rabbits in each of Groups 1, 2, and 9 were necropsied and the panel of 20 organs harvested in compliance with GLP. Three minor abnormalities were found, including two in the FLUZONE™ group 1 (loose stool) and one in MAS-1 placebo group 9 (small lobe of extra-splenic tissue). None of these abnormalities were considered to be related to any of the test materials, nor were they believed to have any bearing on the study outcome. Eleven of the 20 organs collected from each rabbit in groups 1, 2 and 9 were weighed prior to fixation. The organ weights, the organ to body weight ratios, and the organ to brain weight ratios were compared between the three groups. No statistically significant differences between the groups were found in these comparisons, with three exceptions: First: the mandibular lymph nodes, which are distal to the injection sites in the rear legs, were heavier in group 1 than in groups 2 or 9 rabbits. Second: the right (but not left) popliteal lymph nodes were slightly larger in group 9 than in group 2 rabbits. Third: Brain/body weight ratio was statistically smaller in group 2 than group 9 rabbits. The actual brain weights between groups 2 and 9 were not different and apparent differences in brain/body weight ratio can be attributed to the differences in overall body weights between Groups 2 and 9. None of these observations were considered to be significant to the safety of any of the test articles.

Histopathology: Histopathology on the 20 organs collected from groups 1, 2, and 9 rabbits was performed in compliance with GLP. Occasional instances of cellular infiltrates and/or congestion noted for some organs were concluded to be typical background findings. This study confirmed the expected lack of systemic toxicity and found no evidence of histomorphologic differences between rabbits treated with the adjuvanted vaccine of the invention at 15 µg/H antigen and rabbits treated with either FLUZONE™ or MAS-1 placebo.

Injection site tolerance: Immediately after sacrifice of the rabbits on study day 84, injection sites were scored visually (macroscopic) and biopsy specimens collected. The biopsies were subsequently studied for histopathology and graded by a Board Certified veterinary pathologist. Visual and histology evaluations are presented in Table 8.

TABLE 8

Visual and Histology Scores at sites 1 and 2 after IM injection in rabbit thigh muscle

| | | | | Injection site 1 (Day 0 Inj) | | | | Injection site 2 (Day 28 Inj) | | | |
| --- | --- | --- | --- | --- | --- | --- | --- | --- | --- | --- | --- |
| | Vaccine | Dose | Vol | Visual | | Histology | | Visual | | Histology | |
| Grp | TIV | µg/H | mL | Mean | Range | Mean | Range | Mean | Range | Mean | Range |
| 1 | Fluzone | 15.0 | 0.5 | 0 | 0 | 0 | 0 | 0 | 0 | 0 | 0 |
| 2 | MAS-1/TIV | 15.0[a] | 0.3 | 0 | 0 | 1.5 | 0-2.5 | 0.4 | 0-1 | 0.5 | 0-1.5 |
| 3 | MAS-1/TIV | 5.0[b] | 0.3 | 0 | 0 | 0 | 0 | 0.3 | 0-1 | 1.5 | 0-2.5 |
| 4 | MAS-1/TIV | 5.0[a] | 0.3 | 0.1 | 0-0.5 | 0 | 0 | 0.7 | 0-1 | 1.4 | 0-3 |
| 5 | MAS-1/TIV | 5.0[c] | 0.1 | 0 | 0 | 0 | 0 | 0.1 | 0-0.5 | 1.0 | 0-3 |
| 6 | MAS-1/TIV | 1.67[a] | 0.3 | 0 | 0 | 0 | 0 | 0.5 | 0-1 | 1.5 | 0-3 |
| 7 | MAS-1/TIV | 1.67[a] | 0.1 | 0 | 0 | 0 | 0 | 0.4 | 0-1 | 1.1 | 0-3 |
| 8 | MAS-1/TIV | 0.56[b] | 0.3 | 0.2 | 0-0.5 | 0 | 0 | 0.3 | 0-1 | 0.7 | 0-2 |
| 9 | Placebo | 0 | 0.3 | 0 | 0 | 0.2 | 0-1 | 0.1 | 0-0.5 | 0.7 | 0-1 |

[a]Emulsified directly to the indicated concentration of H antigen.
[b]Emulsion prepared at strength for Group 2 was diluted 1:3 with placebo emulsion
[c]Same emulsion as that used for Group 2

| Key to visual pathology scores | | Key to histolopathology scores | |
|---|---|---|---|
| Normal tissue | 0-0.5 | Normal tissue or very mild inflammation | 0-0.5 |
| Minimal pathology | 1-1.5 | Mild active or residual chronic pathology | 1-1.5 |
| Moderate pathology | 2-2.5 | Moderate active chronic inflammation | 2-2.5 |
| | | 3 Severe chronic inflammation/pathology | 3 |

Visual injection site scores of ≤1, and histology scores of ≤2 are indicative of a tolerable formulation; some inflammation is anticipated and correlates with the immune response enhanced by the adjuvant. FLUZONE™ was well tolerated at injection sites 1 and 2, but consistent with its lower immune response, only limited inflammation was seen histologically at both sites. MAS-1/TIV was well tolerated both visually and histologically at the site of the first injection. Of the 35 MAS-1/TIV injection sites examined, three (one in Group 4, two in Group 8) received visual scores of 0.5, indicating barely discernable difference between the injection site and surrounding muscle tissue. The remaining 32 MAS-1/TIV and all 5 FLUZON™ and 5 MAS-1 placebo first injection sites appeared normal. The second MAS-1/TIV injection was more reactogenic, with 7/35 sites at 0.5, 10/35 sites at 1.0 and 18/35 with 0 visual scores. The second MAS-1 placebo injection had 1/5 sites at 0.5 with 4/5 at a 0 visual score. All second injection sites with FLUZONE™ had 0 visual score.

The macroscopic injection site scores were generally supported by histological examinations of biopsy specimens. Thus, histopathology was not observed at the first injection site in any rabbits except for those in group 2, where moderate microscopic reactions were noted in two rabbits and mild reactions seen in two others. Increased inflammation was found at the second injection site for all MAS-1/TIV formulations, with scores ranging from 0 to 3. Mild inflammation at site two was noted in two rabbits receiving MAS-1 placebo, while FLUZONE™ did not elicit inflammation at the second injection sites.

Both visual and histopathology assessments support a single injection regimen anticipated for MAS-1 adjuvanted TIV to be administered IM as a prophylactic influenza vaccine in humans at doses of 15 μg/H antigen or less.

EXAMPLE 7

Preparation of POU Vaccine Formulation from Commercial Seasonal Influenza Vaccine Supplies.

Preparation of the vaccine miniemulsions of the invention requires mixing and emulsification the aqueous phase containing the protein antigen with oily vehicle. Standard stock influenza vaccine contains 30 μg/mL (TIV 30) of each H antigen or TIV containing higher concentrations, (a 4-fold higher strength seasonal TIV vaccine for the elderly comprising 120 μg/mL (TIV 120) Sanofi Pasteur) may be used for each H antigen. The vaccines of the invention are preferably about a 30:70 (w/w) water-in-oil emulsion. To produce POU vaccine formulations of the invention for clinical purposes so as to provide doses at 1.0, 3.0, and 5.0±15% μg/H antigen, the TIV 30 and TIV 120 vaccines are combined with MAS-1 vehicle as indicated in the schematic shown in Table 9.

POU Process Outline:

Step 1: In each case, for 1, 3 and 5 μg/H antigen doses in MAS-1 formulation, 0.5 mL of FLUZONE™ TIV 30 and TIV 120 are removed from the FLUZONE™ vials according to the schema A and B shown in Table 9.

Step 2; The TIV aqueous phase solutions are then transferred by injection into single use, pre-filled sterile PBS vials and mixed by hand.

Step 3: In each case, 0.5 mL of each [diluted] aqueous phase is then transferred by injection into single use pre-filled, sterile vials containing 1.2 g of MAS-1 adjuvant. The vial contents are mixed by shaking vigorously for 30 seconds to produce a milky pre-emulsion.

Step 4: The aqueous and MAS-1 pre-emulsion mixture is transferred into a 2.0 ml syringe and emulsified using the double syringe method.

TABLE 9

POU formulations at 1, 3, and 5 ± 15% μg/H antigen for clinical purposes

| | | | MAS-1/TIV | | |
|---|---|---|---|---|---|
| Step | Dose | μg | 1.0 μg/H | 3.0 μg/H | 5.0 μg/H |
| A1 | TIV 30 | mL | 0.5 | 0.5 | 0.5 |
| A2 | PBS for dilution | mL | 1.0 | — | — |
| A3 | Diluted Aq. Phase | mL | 0.5 | 0.5 | 0.5 |
| | MAS-1 | g | 1.2 | 1.2 | 1.2 |
| A4 | MAS-1/TIV yield | mL | 1.9 | 1.9 | 1.9 |
| | Dose Vol | mL | 0.3 | 0.3 | 0.5 |
| B1 | TIV 120 | mL | 0.5 | 0.5 | 0.5 |
| B2 | PBS for dilution | mL | 1.67 | 0.23 | — |
| B3 | Diluted Aq. Phase | mL | 0.5 | 0.5 | 0.5 |
| | MAS-1 | g | 1.2 | 1.2 | 1.2 |
| B4 | MAS-1/TIV yield | mL | 1.9 | 1.9 | 1.9 |
| | Dose vol | mL | 0.1 | 0.1 | 0.12 |

Based on the results in rabbits (Table 6A) showing statistical equivalency between as low as 0.56 μg/H antigen in MAS-1/TIV and 15 μg/H antigen in standard TIV, we anticipate that from about 1 to 5 μg/H antigen dose in formulated in MAS-1 delivered in either 0.1 mL or 0.3 mL should be optimal for use in the elderly human patients.

POU Syringe Hand Mixing Process: At 1 to 2 mL scale, the mixing procedure takes 90-120 seconds using a pre-set number of cycles. The geometry of the syringe method and flow characteristics are critical to successful emulsification. The emulsion pre-mix is drawn into a 2 mL Norm-Ject syringe and then attached to a 3-way stopcock. A second 2 mL syringe is then attached to the stopcock at 90°. The assembly is clasped firmly around the 3-way stopcock. The pre-emulsion is passed from one syringe to the second by carefully depressing the first syringe plunger with the palm of the other hand. This constitutes 1 pass or cycle. Full emulsification is then achieved by completing 125 cycles within 90-120 (or 150 seconds at 5 mL scale). (Syringes—2 to 5 mL Norm-Ject, sterile, single-use, all plastic Tuberculin, Air-tite Products Co. Inc, VA USA; Henke Sass Wolf GMBH, Tuttlingen, Germany; Kruuse UK Ltd, UK; Syringe needles—18 or 21 gauge, sterile, single use; 3-way stopcock, lipid resistant, Vygon Corp, catalog number 876.00)

Typically the emulsions are expelled into a clean sterile vial and can be transferred from the pharmacy to the patient area prior to removing the prescribed injection volume. The POU method is effective for producing from 1 to 5 mL of adjuvanted vaccine that should remain stable for at least 24 hours at ambient temperature (Tables 3 and 4). The low viscosity, free flowing emulsions enable accurate low volume dosing with as little as 0.1 to 0.3 mL injection volumes. This means that multiple (from 3 to 10 at 1 mL scale to 15 to 50 at 5 mL scale) POU doses of the adjuvanted influenza vaccine of the invention can be simply and quickly provided by this POU method, particularly useful in the event of a pandemic influenza outbreak.

The POU process is useful in epidemic emergency response situations where there is a need for a potent adjuvant system that can be formulated and administered with antigens that are in short supply. The oil component of the emulsion can be stockpiled with kits such as described above, comprising syringes, vials, stopcocks, etc. and distributed independently of the required vaccine antigen, which can subsequently be delivered as it becomes available. This type of POU system can be particularly useful for a rapid response in epidemic and biodefense situations where there is very short time period between the outbreak of the infectious agent and the identification of an effective target antigen and its production in sufficient quantity for vaccination of large populations.

A kit useful for the point-of-use administration of a water-in-oil emulsion vaccine against an infectious agent comprises a sterile vial of an adjuvant oil, a sterile vial of aqueous PBS for combining with an infectious agent antigen, two sterile syringes, a lipid resistant three-way stopcock, a 21 gauge sterile needle, a 25 gauge sterile needle and a sterile vial for storing the formulated water-in-oil emulsion vaccine. The adjuvant oil should be useful with a wide range of protein antigens. In one embodiment of the invention the adjuvant oil comprises mannide monooleate, squalene and squalane. Other oil adjuvants may be formulated as described above. The MAS-1 adjuvant available from Mercia Pharma, Inc. may be used as the adjuvant oil for the vaccines of the invention. Other oil adjuvants such as the Montanide adjuvants available from SEPPIC, SA, Paris, France, that are not mineral oil based but are comprised of animal or vegetable sourced oils may also be used to formulate vaccines of the invention according to the methods described herein. The kits may be used with a wide range of influenza antigens or antigens of other infectious agents or combinations of such antigens, including toxins derived from said pathogens.

That which is claimed:

1. A nanoparticle water-in-oil adjuvant vaccine comprising one or more protein influenza antigens with enhanced immunopotency to the protein influenza antigens compared to an unadjuvanted vaccine comprising the same or a higher concentration of the protein influenza antigens; wherein the vaccine comprises:
   a nanoparticulate water-in-oil emulsion having a viscosity of 100 cP or less;
   an aqueous phase which comprises about 25% to about 35% by weight of the emulsion, which aqueous phase is in the form of globules of a median diameter from about 0.3 μm to about 1 μm, and contains said one or more influenza antigens; and
   an oil phase which comprises from about 65% to about 75% by weight of the emulsion, which oil phase contains from about 85% to about 90% of squalene and squalane, from about 9% to about 12% of mannide monooleate, and from about 0.5% to about 0.7% of polyoxyl-40-hydrogenated castor oil, each by weight of the oil phase;
   wherein:
   (i) said vaccine has enhanced cross-reactivity to protein influenza antigens not contained in the vaccine as compared to an unadjuvanted vaccine consisting essentially of the protein antigens;
   (ii) said vaccine has increased response rate in elderly and immunocompromised subjects as compared to an unadjuvanted vaccine consisting essentially of the protein antigens; and
   (iii) said vaccine provides an extended period of protective antibody titers as compared to an unadjuvanted vaccine consisting essentially of the protein antigens.

2. The composition of claim 1, wherein said squalene comprises a range from about 40% to about 60% by weight of the oil phase.

3. The composition of claim 1, wherein said squalane comprises a range from about 40% to about 60% by weight of the oil phase.

4. The composition of claim 1 wherein said squalene and said squalane are in a ratio of about 1:1 by weight.

5. The composition of claim 1, wherein said nanoparticulate water in oil emulsion vaccine comprises an aqueous phase from about 27% to about 33% by weight.

6. The composition of claim 1, wherein the median globule size is about 300 nm.

7. The composition of claim 1, wherein said water in oil emulsion vaccine further comprises a protein solubilizer.

8. The composition of claim 1, wherein said protein solubilizer is urea or DMSO.

9. The composition of claim 1 wherein the influenza antigen comprises components derived from more than one influenza strain.

10. The composition of claim 1, wherein vaccine composition comprises a nanoparticulate water-in-oil emulsion having a viscosity of about 86 cP.

11. The composition of claim 1 wherein the vaccine is effective to enhance durable cross-reactive immunoprotection towards influenza virus strains not included in the vaccine.

12. A method for influenza prophylaxis, the method comprising administering an effective amount of the vaccine of claim 1 to a patient in need thereof.

13. The method of claim 12, wherein the vaccine is effective to enhance immunopotency for influenza antigens in the vaccine relative to an unadjuvanted trivalent inactivated vaccine containing the same antigens, where the concentrations are the same in the vaccine and in the unadjuvanted trivalent inactivated vaccine.

14. The method of claim 13, wherein said squalene and said squalane are in a ratio of about 1:1 by weight.

15. The method of claim 13, wherein said water in oil emulsion vaccine further comprises a protein solubilizer.

16. The method of claim 15, wherein said protein solubilizer is urea or DMSO.

17. The method of claim 12, wherein the vaccine is effective to extend the period for maintaining protective HAI titers over the period induced by a 15 μm/H antigen dose of an unadjuvanted trivalent inactivated vaccine containing influenza antigens where the concentrations of the antigens are the same in the vaccine and in the unadjuvanted trivalent inactivated vaccine.

18. The method of claim 17, wherein said squalene and said squalane are in a ratio of about 1:1 by weight.

19. The method of claim 17, wherein said water in oil emulsion vaccine further comprises a protein solubilizer.

20. The method of claim 17 wherein said protein solubilizer is urea or DMSO.

* * * * *